United States Patent
Fedorov et al.

(10) Patent No.: US 9,650,671 B2
(45) Date of Patent: *May 16, 2017

(54) SEQUENCING REACTIONS WITH LITHIUM FOR PULSE WIDTH CONTROL

(71) Applicant: Pacific Biosciences of California, Inc., Menlo Park, CA (US)

(72) Inventors: Andrei Fedorov, San Bruno, CA (US); John Lyle, Fremont, CA (US); Keith Bjornson, Fremont, CA (US); Jeremiah Hanes, Menlo Park, CA (US)

(73) Assignee: Pacific Biosciences of California, Inc., Menlo Park, CA (US)

(*) Notice: Subject to any disclaimer, the term of this patent is extended or adjusted under 35 U.S.C. 154(b) by 105 days.

This patent is subject to a terminal disclaimer.

(21) Appl. No.: 14/642,307

(22) Filed: Mar. 9, 2015

(65) Prior Publication Data

US 2015/0203908 A1 Jul. 23, 2015

Related U.S. Application Data

(63) Continuation of application No. 13/177,775, filed on Jul. 7, 2011, now Pat. No. 8,986,930.

(60) Provisional application No. 61/363,591, filed on Jul. 12, 2010.

(51) Int. Cl.
C12Q 1/68 (2006.01)
C07H 21/02 (2006.01)

(52) U.S. Cl.
CPC .................. C12Q 1/6869 (2013.01)

(58) Field of Classification Search
CPC ............ C12C 1/6869; C12C 2527/125; C12C 2563/137
See application file for complete search history.

(56) References Cited

U.S. PATENT DOCUMENTS

| | | | |
|---|---|---|---|
| 5,001,050 A | 3/1991 | Blanco et al. | |
| 5,409,811 A | 4/1995 | Tabor et al. | |
| 6,165,765 A | 12/2000 | Hong et al. | |
| 6,399,320 B1 | 6/2002 | Markau et al. | |
| 6,399,335 B1 | 6/2002 | Kao et al. | |
| 6,447,724 B1 | 9/2002 | Jensen et al. | |
| 6,610,486 B1 | 8/2003 | Dahlhauser | |
| 6,762,048 B2 | 7/2004 | Williams | |
| 6,787,308 B2 | 9/2004 | Balasubramanian et al. | |
| 6,917,726 B2 | 7/2005 | Levene et al. | |
| 6,936,702 B2 | 8/2005 | Williams et al. | |
| 7,041,812 B2 | 5/2006 | Kumar et al. | |
| 7,056,661 B2 | 6/2006 | Korlach et al. | |
| 7,057,026 B2 | 6/2006 | Barnes et al. | |
| 7,315,019 B2 | 1/2008 | Turner et al. | |
| 2006/0051807 A1 | 3/2006 | Fuller | |
| 2006/0063173 A1 | 3/2006 | Williams et al. | |
| 2007/0036511 A1 | 2/2007 | Lundquist et al. | |
| 2007/0077564 A1 | 4/2007 | Roitman et al. | |
| 2007/0188750 A1 | 8/2007 | Lundquist et al. | |
| 2007/0196846 A1 | 8/2007 | Hanzel et al. | |
| 2007/0206187 A1 | 9/2007 | Lundquist et al. | |
| 2008/0030628 A1 | 2/2008 | Lundquist et al. | |
| 2008/0108082 A1 | 5/2008 | Rank et al. | |
| 2008/0212960 A1 | 9/2008 | Lundquist et al. | |
| 2008/0299565 A1 | 12/2008 | Schneider et al. | |
| 2009/0029385 A1 | 1/2009 | Christians et al. | |
| 2009/0280538 A1 | 11/2009 | Patel et al. | |
| 2009/0286245 A1 | 11/2009 | Bjornson et al. | |
| 2010/0112645 A1 | 5/2010 | Clark et al. | |

FOREIGN PATENT DOCUMENTS

| | | |
|---|---|---|
| WO | 02086088 A2 | 10/2002 |
| WO | 2007075987 A2 | 7/2007 |
| WO | 2007076057 A2 | 7/2007 |
| WO | 2007123763 A2 | 11/2007 |
| WO | 2007137060 A2 | 11/2007 |
| WO | 2008154317 A1 | 12/2008 |
| WO | 2009102470 A2 | 8/2009 |
| WO | 2009145828 A2 | 12/2009 |

OTHER PUBLICATIONS

Arndt et al. "Insight into the catalytic mechanism of DNA polymerase Beta: Structures of intermediate complexes" Biochem (2001) 40:5368-5375.
Arnold, J.J. et al, "Polivirus RNA-dependent RNA polymerase(3pol): pre-steady-state kinetic analysis of ribonucleotide incorporation in the presence of Mn2+" Biochem (2004) 43(18):5138-5148.
Bakhtina et al. "Use of viscogens dNTPaS, and Rhodium (III) as probes in stopped-flow experiments to obtain new evidence for the mechanism of catalysis by DNA polymerase" Biochem (2005) 44(13):5177-5187.
Berman et al. "Structures of phi29 polymerase complexes with substrate: the mechanism of translocation in polymerases" EMBO J (2007) 26:3494-3505.
Blanco et al. "Mutational analysis of bacteriophage phi29 DNA polymerase" Meth in Enzym (1995) 262:283-294.
Blasco et al. "phi29 DNA polymerase active site" J Biol Chem (1993) 268(22):16763-16770.
Castro et al. "Two proton transfers in the transition state for nucleotidyl transfer catalyzed by RNA and DNA-dependent RNA and DNA polymerases" PNAS (2007) 104(11):4267-4272.
Eid et al. "Real-time DNA sequencing from single polymerase molecules" Science (2009) 323(5910):133-138.
Korlach et al., "Long, Processive Enzymatic DNA Synthesis Using 100% Dye-Labeled Terminal Phosphate-Linked Nucleotides" Nucleosides, and Nucleotides and Nucleic Acids (2008) 27:1072-1083.

(Continued)

Primary Examiner — Teresa Strzelecka
(74) Attorney, Agent, or Firm — David C. Scherer; Robert H. Reamey

(57) ABSTRACT

Compositions, kits, methods and systems for single molecule nucleotide sequencing comprising producing polymerase reactions having lithium that control the median pulse width for incorporated nucleotides are disclosed. The levels of lithium are used to control pulse width while allowing other sequencing parameters to remain within a desirable range.

18 Claims, 8 Drawing Sheets

(56) References Cited

OTHER PUBLICATIONS

Korlach et al., "Selective aluminum passivation for targeted immobilization of single DNA polymerase molecules in zero-mode waveguide structures" PNAS (2008) 105(4):1176-1181.
Levene et al., "Zero-mode waveguides for single moledule analysis at high concentrations" Science (2003) 299:682-686.
Lu et al. "Monovalent Cation Binding by Curved DNA Molecules Containing Variable Numbers of A-Tracts," Biophysical Journ (2008) 94:1719-1735.
Lundquist et al. "Parallel confocal detection of single molecules in real time" Opt Lett (2008) 33(9):1026-1028.
McFail-Isom et al. "DNA Structure: Cations in Charge?" Current Opinion Structural Biology (1999) 9:298-304.
Miyake, T. et al., "Real-Time Imaging of Single-Molecule Fluorescence with a Zero-Mode Waveguide for the Analysis of Protein-Protein Interaction" Anal Chem (2008) 80:6018-6022.
Nicholson et al. "Enhanced protein thermostability from designed mutations that interact with alpha-helix dipoles" Nature (1988) 336:651-656.
Rechkunova, N.I. et al, "Thermostable DNA polymerase from Thermus thermophilus B35: influence of divalent metal ions on the interaction with deoxynucleoside triphosphates" Biochem (2000) 65(5):609-614.
Schultze et al. "The effect of sodium, potassium and ammonium ions on the conformation of the dimeric quadruplex formed by the Oxytricha nova telomere repeat oligonucleotide d(G4T4G4)." Nucleic Acid Research (1999) 27(15): 3018-28.
Shui et al. "Structure of the Potassium Form of CGCGAATTCGCG: DNA Deformation by Electrostatic Collapse around Inorganic Cations." Biochemistry (1998) 37:16877-87.
Soengas et al. "Site directed mutaenesis at the Exo III motif of phi29 DNA polymerase. Overlappying structural domains for the 3'-5' exonuclease and strand-displacement activities" EMBO J (1992) 11:4227-4237.
Tang et al. "Mismatched dNTP incorporation by DNA polymerase beta does not proceed via globally different conformational pathways" Nucl Acids Res (2008) 36(9):2948-2957.
Tock, M.R. et al. "Dynamic evidence for metal ion catalysis in the reaction mediated by a flap endonuclease" EMBO J. (2003) 22(5):995-1004.
Truniger et al. "A positively charged residue of phi29 DNA polymerase, highly conserved in DNA polymerases from families A and B, is involved in binding the incoming nucleotide" Nuc Acids Res (2002) 30(7):1483-1494.
Vlassakis et al. "Probing the Mechanical Stability of DNA in the Presence of Monovalent Cations." JACS (2008) 130:5004-5005.
Xie, S. et al. "Single-molecule enzymology" J Biol Chem (1999) 274(23):15967-15970.
Zhou et al. "Kinetic analysis of sequential multistep reactions" J Phys Chem B (2007) 111:13600-13610.
Bollum F.J. "Calf Thymus Polymerase," Journ Biol Chem (1960) 235(8):2399-2403.
Klenow et al. "Effect of Monovalent Cations on the Activity of the DNA Polymerase of *Escherichia coli* B," European J. Biochem (1969) 9:133-141.
Palan et al. "Specific Effect of Zinc Ions on DNA Polymerase Activity on Avian Myeloblastosis Virus," Molecular & Cellular Biocemisty (1978) 21(2):67-69.
International Search Report and Written Opinion dated Feb. 27, 2012 from related case PCT/US2011/043227.
International Preliminary Report on Patentability dated Jan. 24, 2013 from related case PCT/US2011/043227.

SEQUENCING REACTIONS WITH LITHIUM FOR PULSE WIDTH CONTROL

CROSS-REFERENCE TO RELATED APPLICATIONS

This application is a continuation application of U.S. patent application Ser. No. 13/177,775 filed Jul. 7, 2011 which claims priority and benefit of Provisional Patent Application 61/363,591 filed on Jul. 12, 2010, the full disclosures of which is incorporated by reference herein in its entirety.

STATEMENT REGARDING FEDERALLY SPONSORED RESEARCH

Not Applicable.

Incorporation-by-Reference of Material Submitted by U.S.P.T.O. eFS-WEB

The instant application contains a Sequence Listing which is being submitted in computer readable form via the United States Patent and Trademark Office eFS-WEB system, and is hereby incorporated by reference in its entirety for all purposes. The txt file submitted herewith contains only 6 KB file (01012902_2015-03-09_SequenceListing.txt).

BACKGROUND OF THE INVENTION

The ability to read the genetic code has opened countless opportunities to benefit humankind Whether it involves the improvement of food crops and livestock used for food, the identification of the causes of disease, the generation of targeted therapeutic methods and compositions, or simply the better understanding of what makes us who we are, a fundamental understanding of the blueprints of life is an integral and necessary component.

A variety of techniques and processes have been developed to obtain genetic information, including broad genetic profiling or identifying patterns of discrete markers in genetic codes and nucleotide level sequencing of entire genomes. With respect to determination of genetic sequences, while techniques have been developed to read, at the nucleotide level, a genetic sequence, such methods can be time-consuming and extremely costly.

Approaches have been developed to sequence genetic material with improved speed and reduced costs. Many of these methods rely upon the identification of nucleotides being incorporated by a polymerization enzyme during a template sequence-dependent nucleic acid synthesis reaction. In particular, by identifying nucleotides incorporated against a complementary template nucleic acid strand, one can identify the sequence of nucleotides in the template strand. A variety of such methods have been previously described. These methods include iterative processes where individual nucleotides are added one at a time, washed to remove free, unincorporated nucleotides, identified, and washed again to remove any terminator groups and labeling components before an additional nucleotide is added. Still other methods employ the "real-time" detection of incorporation events, where the act of incorporation gives rise to a signaling event that can be detected. In particularly elegant methods, labeling components are coupled to portions of the nucleotides that are removed during the incorporation event, eliminating any need to remove such labeling components before the next nucleotide is added (See, e.g., Eid, J. et al., Science, 323(5910), 133-138 (2009)).

In any of the enzyme mediated template-dependent processes, the overall fidelity, processivity and/or accuracy of the incorporation process can have direct impacts on the sequence identification process, e.g., lower accuracy may require multiple fold coverage to identify the sequence with a high level of confidence.

The present invention provides methods, systems and compositions that provide for increased performance of such polymerization based sequencing methods, among other benefits.

BRIEF SUMMARY OF THE INVENTION

The present invention is generally directed to enzyme reactions, and in particular, nucleic acid synthesis compositions, systems, and methods that can be used to observe the incorporation of nucleic acids into a growing strand as they are added in order to determine nucleic acid sequences. We have unexpectedly found that monovalent cations such as alkali metals, when added to the sequencing reaction in the proper amount, can improve the sequencing accuracy by affecting the pulse width that corresponds with the time in which a nucleotide analog is associated with the polymerase enzyme prior to incorporation of the nucleotide analog and cleavage of the polyphosphate. We have found that these cations can be used to modulate the kinetics of the polymerase enzyme. In some cases, we have found that we can control the pulse width without adversely significantly affecting other sequencing parameters such as interpulse distance.

One aspect of the invention is a composition for single molecule nucleic acid sequencing comprising: a polymerase enzyme, primer, a template nucleic acid, and a plurality of labeled nucleic acid analogs wherein the composition comprises Li+ at a concentration from about 0.05 mM to about 20 mM; Na+ at a concentration from 1 mM-400 mM, K+ at a concentration from about 100 mM to about 400 mM, Rb+ at a concentration from about 0.1 mM to about 40 mM, or Cs+ at a concentration from about 0.1 mM to about 40 mM.

In some embodiments the single molecule sequencing reaction has a median pulse width between about 10 msec and about 400 msec. In some embodiments the single molecule sequencing reaction has an interpulse distance is from about 300 msec to about 1.5 s. In some embodiments the single molecule sequencing reaction has a median read length greater than about 300 bases. In some embodiments the has both Na+ and Li+, both Li+ and K+, both Na+ and K+, or all three of Li+, Na+ and K+.

In some embodiments the concentration of Li+ is from about 0.1 mM to about 4 mM. In some embodiments the concentration of Na+ is from about 5 mM to about 40 mM. In some embodiments the concentration of K+ is from about 150 mM to about 250 mM. In some embodiments the concentration of Rb+ is from about 1 mM to about 10 mM. In some embodiments the concentration of Cs+ is from about 1 mM to about 10 mM.

In some embodiments the polymerase enzyme, primer, and template nucleic acid comprise a polymerase complex that is immobilized on a surface. In some embodiments the polymerase complex is immobilized onto the surface by attachment to the surface of the polymerase enzyme, the primer, or the template nucleic acid. In some embodiments the polymerase complex is immobilized in a zero mode waveguide.

In some embodiments the plurality of nucleic acids comprise nucleic acids labeled on the phosphate portion of the nucleotide such that the label dissociates upon incorporation into the growing strand.

One aspect of the invention is composition for single molecule nucleic acid sequencing comprising: a polymerase enzyme, primer, a template nucleic acid, and a plurality of labeled nucleic acid analogs wherein the composition comprises a mixture of alkali metals comprising K+ at a concentration of from about 50 mM to about 300 mM, and another alkali metal cation at a concentration from about 0.05 mM to about 100 mM.

In some embodiments the other alkali metal cation is Li+ at a concentration of from about 0.05 mM and about 40 mM. In some embodiments the other alkali metal cation is Li+ at a concentration of from about 0.1 mM to about 4 mM In some embodiments the other alkali metal cation is Na+ at a concentration of from about 1 mM and about 100 mM. In some embodiments the other alkali metal cation is Na+ at a concentration of from about 5 mM to about 40 mM. In some embodiments the other alkali metal cation is Rb+ at a concentration of from about 0.1 mM and about 40 mM. In some embodiments the other alkali metal cation is Rb+ at a concentration of from about 1 mM and about 10 mM. In some embodiments the other alkali metal cation is Cs+ at a concentration of from about 0.1 mM and about 40 mM. In some embodiments the other alkali metal cation is Cs+ at a concentration of from about 1 mM and about 10 mM.

One aspect of the invention comprises a use of an alkali metal to control the pulse width in a single molecule sequencing reaction comprising: providing a reaction mixture comprising a polymerase enzyme, primer, a template nucleic acid, and a plurality of labeled nucleic acid analogs wherein the composition comprises an alkali metal cation at a concentration of between about 0.5 mM and about 300 mM.

In some embodiments the other alkali metal cation is Li+ at a concentration of between about 0.05 mM and about 20 mM. In some embodiments the other alkali metal cation is Na+ at a concentration of between about 1 mM and about 100 mM. In some embodiments the other alkali metal cation is Rb+ at a concentration of between about 0.1 mM and about 40 mM. In some embodiments the other alkali metal cation is Cs+ at a concentration of between about 0.1 mM and about 40 mM.

One aspect of the invention is a method for single molecule sequencing comprising: immobilizing a plurality of polymerase enzyme complexes, each having a polymerase enzyme, a primer, and a template nucleic acid onto a substrate; contacting the polymerase enzyme complexes with a sequencing reaction mixture comprising the components required for the polymerase to synthesize a growing nucleic acid strand; wherein the sequencing reaction mixture comprises labeled nucleotide analogs and comprises Li+ at a concentration from about 0.05 mM to about 20 mM; Na+ at a concentration from 1-400 mM; K+ at a concentration from about 100 mM to about 400 mM; Rb+ at a concentration from about 0.1 mM to about 40 mM; or Cs+ at a concentration from about 0.1 mM to about 40 mM and observing the association of the labeled nucleotide analogs with the polymerase complex over time to determine a sequence of the template nucleic acid.

In some embodiments the amount of the Li+, Na+, K+, Rb+, or Cs+ is selected to provide a median pulse width from about 10 msec to about 400 msec.

One aspect of the invention is a method for single molecule sequencing comprising: immobilizing a plurality of polymerase enzyme complexes, each having a polymerase enzyme, a primer, and a template nucleic acid onto a substrate; contacting the polymerase enzyme complexes with a sequencing reaction mixture comprising the components required for the polymerase to synthesize a growing nucleic acid strand; wherein the sequencing reaction mixture comprises labeled nucleotide analogs and comprises Li+, Na+, Rb+, or Cs+ at a concentration of from about 0.05 mM and about 100 mM and observing a series of pulses indicative of the association of the labeled nucleotide analogs with the polymerase complex over time to determine a sequence of the template nucleic acid; wherein the median pulse width is between about 10 msec and about 400 msec.

In some embodiments the mixture further comprises K+ at a concentration from about 50 mM to about 400 mM. In some embodiments the median pulse width is between 50 msec and about 200 msec. In some embodiments the sequencing reaction mixture comprises a plurality of labeled nucleic acid analogs, and the nucleic acid analogs are labeled such that the label is cleaved upon incorporation of the nucleic acid analog into the growing strand, the observed pulses corresponding to the time period when the labeled nucleic acid is associated with the polymerase enzyme complex.

In some embodiments the polymerase enzyme complex is immobilized onto a substrate. In some embodiments the polymerase enzyme complex is immobilized within a confined volume. In some embodiments the confined volume comprises a zero mode waveguide.

DETAILED DESCRIPTION OF THE INVENTION

Figure 1:
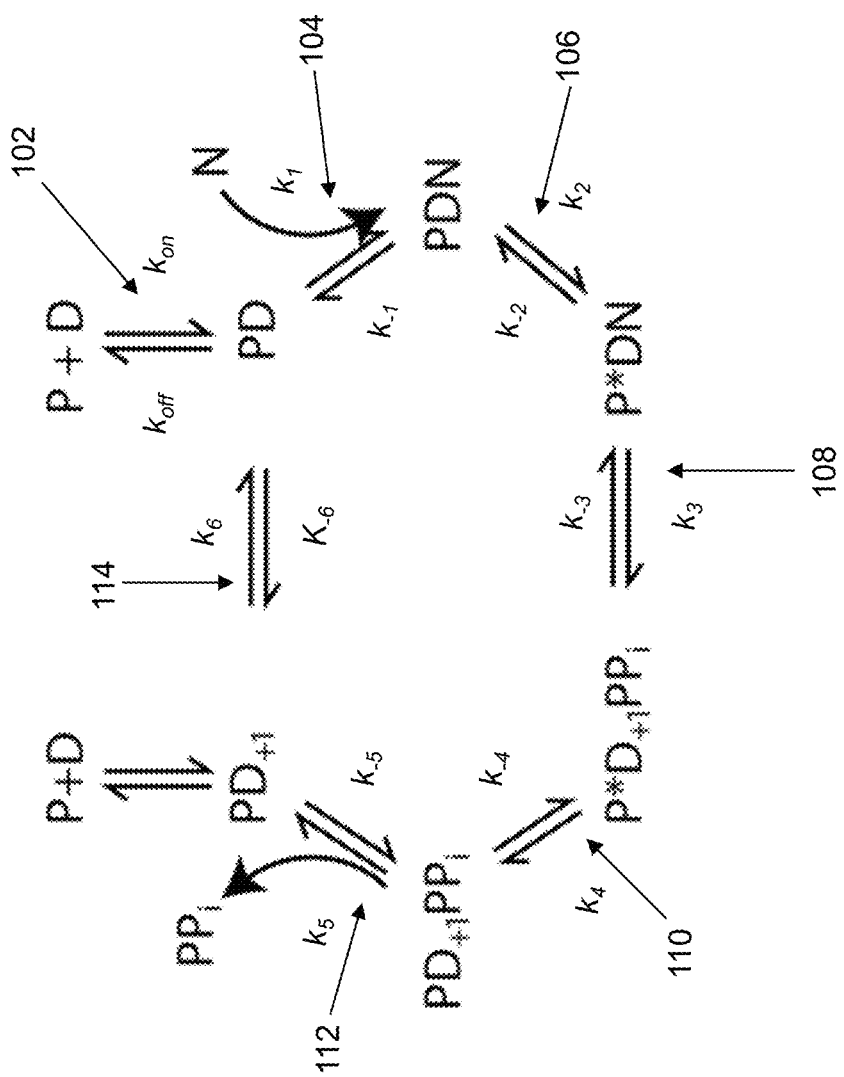
FIG. 1 is a schematic illustration of the reaction cycle for polymerase-mediated nucleic acid primer extension.

The present invention is generally directed to improved enzyme reaction compositions, methods, and systems for sequencing nucleic acid molecules. In particular, the invention relates to improved single molecule real time sequencing. Such sequencing involves observing a polymerase enzyme as it adds nucleotides to a growing nucleic acid strand. By monitoring the addition of the nucleotides or nucleotide analogs and identifying each nucleotide as it is added, the sequence of a template nucleic acid, to which the polymerase is bound, can be determined.

For example, Eid, J. et al., Science, 323(5910), 133-138 (2009), describes how the incorporation of specific nucleotides can be determined by observing bright pulses corresponding to nucleotide-polymer association and dark phases corresponding to the time between incorporation of one nucleotide and the association of another nucleotide analog with the polymerase enzyme. In these systems, each of four nucleotide analogs corresponding to A, G, T, and C is labeled with a different fluorescent dye, each with a characteristic spectral output. The labels are attached to the polyphosphate portion of the nucleotide analog which is cleaved upon incorporation of the nucleotide into the growing strand. The polymerase, along with the corresponding template nucleic acid and primer, is immobilized onto a surface such that signals corresponding to that polymerase can be observed independently of other polymerases in the system. When a nucleotide analog enters the active site of the polymerase, the label on the nucleotide can be observed. If the nucleotide analog is the correct (cognate) nucleotide analog, the enzyme will add the nucleotide analog to the growing strand, thus cleaving and releasing the polyphosphate and dye. The release of the dye will result in the signal going from bright to dark. The characteristic signal of incorporation is thus a pulse, whose rise in brightness corresponds to the association of the nucleotide analog, and whose fall in brightness corresponds to the release of the label upon incorporation. The spectrum of the signal can be used to identify which of the four dyes have been incorporated.

The length of the incorporation pulse (the pulse width) is not the same for each incorporation event. Accordingly, in observing a series of pulses from a given polymerase or set of polymerases, a distribution of pulse widths is seen. In some cases, the incorporation event will occur very fast, resulting in a very short pulse. Where the pulse is extremely fast, there is the danger that the pulse will not be recognized, resulting in an error in the determination of the sequence in which an incorporation event occurred, but was not measured. It can therefore be desirable to have a sequencing system in which the number of very short pulses is reduced, reducing the number of bases that are missed and improving the accuracy.

We have unexpectedly found that by adding monovalent cations at the appropriate level, we are able to control the median pulse width, for example increasing the median pulse width in order to lower the number of missed incorporation events. We have found that by varying the concentration of the cations, the median pulse width can be changed, and that the pulse width can be changed without significantly altering other sequencing parameters such as inter-pulse distance and read length. By increasing the median pulse width, the overall accuracy of the system can be improved. Since the pulse width corresponds to the time that the nucleotide analog is associated with the enzyme before cleavage of the polyphosphate and label, the level and type of monovalent cation appear to control the kinetics of the steps corresponding to these events. While in some cases, the pulse width can be varied without making significant changes in other parameters, we have observed that in some cases, the alkali metal cation type and concentration can also be used to modulate other kinetic parameters such as the interpulse distance. The strong dependence of the chemistry rate on the identity of the alkali metal (not just the concentration) implies a direct interaction of the alkali metal with the system and not a simple modulation of the ionic strength (as the addition of salt would most likely be intended to perform).

The methods of the invention allow for tuning the median pulse width to obtain the optimum sequencing results for a given system, e.g. the best accuracy. As was described above, if the median pulse width is too short, a significant number of pulses may not be detected as they will occur to rapidly to be effectively detected. It is also possible for the median pulse width to be too long. For example, extending the pulse width can result in decreased enzyme lifetime, resulting in some cases to lower read lengths. This decreased lifetime can be caused by having the nucleotide analog associated with the enzyme for a longer period of time. While not being bound by theory, it is understood that where the nucleotide has a fluorescent label, the proximity of the label to the enzyme during illumination can result in enzyme degradation. This degradation can occur where the fluorescent analog is in an excited state due to absorption of one or more photons. The excited state can result in the formation of reactive intermediates such as free radicals, radical anions, or radical cations that can react with portions of the enzyme. The reactive intermediates can comprise other molecules in the medium, or can derive from the fluorescent dye molecule itself. The fluorescent dye label can undergo degradation itself from the excited state, producing reactive intermediates from the degradation products of the dye. The presence of other agents, such as oxygen can enhance the rate of degradation and formation of reactive species.

Increased median pulse width can also be undesirable where the where the pulse width is increased so much that there is a significant slowing of the overall reaction, compromising throughput. Thus there is often a desired range of pulse widths that provide for the fewest number of missing peaks while keeping the lifetime of the enzyme long and not significantly lowering the overall reaction rate. In some cases the monovalent cations of the invention are used do produce median pulse widths of greater than about 1 msec, greater than about 10 msec, greater than about 20 msec, or greater than about 50 msec. In some cases, the monovalent cations of the invention are used do produce average pulse widths of less than about 200 msec, less than about 300 msec, less than about 400 msec, or less than about 500 msec. In some cases the monovalent cations of the invention are used do produce average pulse widths of from about 1 msec to about 500 msec, about 10 msec to about 400 msec, about 20 msec to about 200 msec, or about 50 msec to about 200 msec.

We have found that alkali metal cations can be used to vary the incorporation pulse width in accordance with the invention. The monovalent alkali metal cations include lithium (Li+), sodium (Na+), potassium (K+), rubidium (Rb+), cesium (Cs+), francium (Fr+). The concentration required for a given change in median pulse width can vary with the type of alkali metal cation that is used. For example, we have found that Li+ can affect the pulse width at relatively low levels (e.g. on the order of 0.1 mM), while the amount of K+ required to affect the same change is orders of magnitude higher.

It is not only the type of alkali metal cation that is used to control the pulse width but also the amount of the cation that is used. The exact amount that is used can depend on other factors including the type of polymerase enzyme that used, the pH of the medium, the temperature, the type and concentrations of nucleotide analogs that are used, and the type and concentrations of divalent cations such as Mg++, Mn++, or Ca++ that are employed. In general the monovalent cation such as alkali metal cation is present at a concentration from about 0.05 mM to about 400 mM, or from about 1 mM to about 100 mM. In the case of Lithium (Li+), the concentration can be from about 0.05 mM to about 20 mM, or from about 0.1 mM to about 10 mM, or from about 0.1 mM to about 4 mM. For sodium (Na+), the concentration can be from about 1 mM to about 400 mM, from about 2 mM to about 100 mM, or about 5 mM to about 40 mM. For potassium (K+) the concentration can be from about 100 mM to about 400 mM, or from about 100 mM to about 300 mM, or from about 150 M to about 250 mM. In the case of Rubidium (Rb+) or Cesium (Cs+), the concentration can be from about 0.1 mM to about 40 mM or from about 1 mM to about 10 mM.

It has been known in the art to use salts in order to control the ionic strength of the medium in which the polymerase enzyme is active. Controlling the ionic strength can affect the ability of the enzyme to carry out nucleic acid polymerization. In some cases, the salts used to control the ionic strength have included potassium. We have found that in some cases, we can use a mixture of two alkali metal salts in order to independently control the ionic strength of the medium and the pulse width of the incorporation event. For example, we have found that the pulse width is much less sensitive to the concentration of K+ than it is to the concentration of other alkali metal cations such as Li+ and Na+. Thus, one alkali metal cation, such as potassium, can be used to control the ionic strength, while the level of another alkali metal cation can be used to control pulse width. It will be understood that the ionic strength will be affected by all of the cations in the mixture. However, since the amount of the cation needed for controlling pulse width is a relatively small compared to the amount of potassium present and the total ionic strength, the concentration of such cation can be varied either without resulting in much change in ionic strength, or the amount of potassium or other salts can be adjusted to maintain the same ionic strength without significantly influencing the median pulse width.

For example, in some embodiments, the concentration of potassium used, primarily to control the ionic strength is from about 50 mM to about 300 mM, and the concentration of the other alkali metal cation is from about 0.05 mM to about 100 mM. In some cases the reaction mixture comprises K+ from about 50 mM to about 300 mM, and a concentration of Li+ from about 0.05 mM to about 40 mM or about 0.1 mM to about 4 mM. In some cases the reaction mixture comprises K+ from about 50 mM to about 300 mM, and a concentration of Na+ from about 1 mM and about 100 mM or about 5 mM to about 40 mM. In some cases the reaction mixture comprises K+ from about 50 mM to about 300 mM, and a concentration of Rb+ from about 0.1 mM and about 40 mM, or from about 1 mM and about 10 mM. In some cases the reaction mixture comprises K+ from about 50 mM to about 300 mM, and a concentration of Cs+ from about 0.1 mM and about 40 mM, or from about 1 mM and about 10 mM.

While not being bound by theory, it is believed that the changes in pulse width are due to the interactions of the various types of alkali metal cations with the polymerase and with nucleotide analogs, and also through incorporation of the alkali metal cations into the primary and secondary grooves of DNA. It has been shown that the amount and type of alkali metal cation can affect the geometry of DNA molecules in solution by binding into primary and secondary grooves. See, for example Vlassakis et al., Journal of the American Chemical Society, 2008, 130, 5004-5005; Lu et al., Biophysical Journal, 2008, 94, 1719-1725; Shui et al., Biochemistry, 1998, 37, 16877-16887; Schultze et al., Nucleic Acid Research, 199, 27(15), 3018-3028; and McFail-Isom et al. Current Opinion in Structural Biology, 1999, 9, 298-304).

The alkali cations can be introduced as any type of suitable salt. In some cases, the salt comprises a carboxylic acid salt of the alkali metal cation. In some cases, the salt comprises an acetate salt. In some cases, halide salts can be used. In some cases, the anion could be an anion that serves another function in the reaction mixture such as a reducing agent or photodamage control agent.

The invention includes the use of an alkali metal to control the pulse width in a single molecule sequencing reaction. The use can include providing a reaction mixture comprising a polymerase enzyme, primer, a template nucleic acid, and a plurality of labeled nucleic acid analogs under conditions that allow for polymerase mediated synthesis of a growing nucleic acid chain to occur. The pulse width is controlled by varying the concentration of one or more alkali metal cations within the range about 0.5 mM and about 300 mM. A synthesis reaction can be run and monitored at one alkali metal cation concentration, then the concentration of the alkali metal cation can be varied and the synthesis reaction monitored under the second set of conditions. The median pulse width is determined under each set of conditions, typically along with the measurement of other parameters such as the accuracy, read length, and median interpulse distance. This can be repeated at multiple alkali metal cation concentrations to provide a desired median pulse width, accuracy, read length, etc. In some cases, one alkali metal cation, such as K+ will be present at a relatively high level, e.g. 50 mM to 300 mM to control ionic strength, and the amount of another cation such as Li+, Na+, Rb+, or Cs+ will be varied at a lower concentration level such as the levels described above in order to control pulse width. In nucleic acid sequencing, generally four separate channels are monitored—one channel for each of the nucleotide analogs (e.g. A, G, T, C). Where this is the case, the median pulse width in any or all of the four channels can be determined. We have generally found that where the increase in the concentration of an alkali metal cation results in the increase in pulse width in one channel, it also results in the pulse widths in the other three channels.

In some cases, the pulse width can be varied significantly without commensurate changes in other properties such as interpulse distance and read length. For example, as shown below, in some cases pulse widths can be increased by about 79% on average, while the IPD is only increased by 21% and the readlength is only reduced by 25%, resulting in an accuracy increase of 1.5%.

The compositions and methods of the invention can be used to produce a single molecule sequencing reaction having a median pulse width from about 10 msec to about 400 msec and which has a median interpulse distance is from about 300 msec to about 1.5 s. In some cases the single molecule sequencing reaction has a median pulse width of from about 50 msec to about 200 msec and a median interpulse distance is from about 300 msec to about 1.5 s. The compositions and methods of the invention can be used to produce a single molecule sequencing reaction has a median pulse width from about 10 msec to about 400 msec and which has a median read length of greater than about 300 bases. In some cases the single molecule sequencing reaction has a median pulse width of from about 50 msec to about 200 msec and a median read length of greater than about 500 bases. In some cases the single molecule sequencing reaction has a median pulse width of from about 10 msec to about 400 msec and a median read length of greater than about 1,000 bases. The compositions and methods of the invention can be used to produce a single molecule sequencing reaction has a median pulse width from about 10 msec to about 400 msec, and a median interpulse distance is from about 300 msec to about 1.5 s, and a median read length of greater than about 300 bases.

The invention also comprises a method for single molecule sequencing that comprises performing a single molecule sequencing reaction in which a reaction mixture comprises Li+, Na+, Rb+, or Cs+ at a concentration above about 0.05 mM, resulting in a median pulse width is from about 10 msec and about 400 msec, or from about 50 msec and about 200 msec. For example the method can include immobilizing a plurality of polymerase enzyme complexes, each having a polymerase enzyme, a primer, and a template nucleic acid onto a substrate; contacting the polymerase enzyme complexes with a sequencing reaction mixture comprising the components required for the polymerase to synthesize a growing nucleic acid strand; wherein the sequencing reaction mixture comprises labeled nucleotide analogs and comprises Li+, Na+, Rb+, or Cs+ at a concentration of from about 0.05 mM and about 100 mM and observing a series of pulses indicative of the association of the labeled nucleotide analogs with the polymerase complex over time to determine a sequence of the template nucleic acid; wherein the median pulse width is between about 10 msec and about 400 msec.

Systems Exhibiting Two or More Slow Steps

In some cases, the systems that are used in the present invention are those systems that exhibit kinetic mechanisms having two or more slow, kinetically observable, or partially rate-limiting reaction steps within an observable phase of the polymerase reaction. Such systems can be useful for example, in single-molecule, real-time observations of such enzyme activity, which rely, at least in part, on detecting and identifying the enzyme reaction as it is occurring. By designing the reaction system to have two or more partially rate-limiting steps, the relative number of short, difficult to detect, events can be lowered. Enzymatic reactions often occur at rates that can far exceed the speed of a variety of detection systems, e.g., optical detectors. As such, by providing two or more partially rate-limiting steps within a phase of an enzyme reaction, one improves the ability to monitor that reaction using optical detection systems. Two slow-step systems are described, for example, in Published U.S. Patent Application No. 2009/0286245, the full disclosure of which is incorporated by reference herein for all purposes.

One particular exemplary system includes compositions for carrying out single-molecule DNA sequencing. We describe systems that exhibit two slow steps within an observable phase. An observable phase will generally have a time period during which the phase is observable. The time period for a bright phase, for example, can be represented by the pulse width. The time period for a dark phase can be represented, for example, by the interpulse distance. The length of each time period will not be the same for each nucleotide addition, resulting in a distribution of the length of the time periods. In some cases, the time periods with the shortest length will not be detected, leading to errors, for example in single-molecule sequencing. We have found that by designing enzyme systems such as polymerase reaction systems in which there are two slow, or kinetically observable, steps within an observable phase, the relative number of short, unobservable, time periods can be reduced, resulting in a higher proportion of observable sequencing events, and allowing for a more accurate determination of nucleotide sequence. As used herein, an observable phase includes phases that are not directly observable, but can be ascertained by measurements of other, related phases. For example, the lengths of dark phases can be observed by measuring the times between optical pulses corresponding to a related bright optical phase. Also as described herein, a phase which is dark under some labeling conditions can be bright under other labeling conditions.

Polymerase-Mediated Synthesis

In natural polymerase-mediated nucleic acid synthesis, a complex is formed between a polymerase enzyme, a template nucleic acid sequence, and a priming sequence that serves as the point of initiation of the synthetic process. During synthesis, the polymerase samples nucleotide monomers from the reaction mix to determine their complementarity to the next base in the template sequence. When the sampled base is complementary to the next base, it is incorporated into the growing nascent strand. This process continues along the length of the template sequence to effectively duplicate that template. Although described in a simplified schematic fashion, the actual biochemical process of incorporation is relatively complex.

The process can be described as a sequence of steps, wherein each step can be characterized as having a particular forward and reverse reaction rate that can be represented by a rate constant. One representation of the incorporation biochemistry is provided in FIG. 1. It is to be understood that the scheme shown in FIG. 1 does not provide a unique representation of the process. In some cases, the process can be described using fewer steps. For example, the process is sometimes represented without inclusion of the enzyme isomerization steps 106 and 110. Alternatively, the process can be represented by including additional steps such as cofactor binding or internal enzyme rearrangements. Generally, steps which can be slow, and thus limit the rate of reaction will tend to be included.

As shown in FIG. 1, the synthesis process begins with the binding of the primed nucleic acid template (D) to the polymerase (P) at step 102. Nucleotide (N) binding with the complex occurs at step 104. Step 106 represents the isomerization of the polymerase from the open to closed configuration. Step 108 is the chemistry step where the nucleotide is incorporated into the growing strand of the nucleic acid being synthesized. At step 110, polymerase isomerization occurs from the closed to the open position. The polyphosphate component that is cleaved upon incorporation is released from the complex at step 112. The polymerase then translocates on the template at step 114. As shown, the various steps can include reversible paths and may be characterized by the reaction constants shown in FIG. 1 where:

$k_{on}/k_{off}$=DNA binding/release;
$k_1/k_{-1}$=nucleotide binding/release;
$k_2/k_{-2}$=polymerase isomerization (open/closed);
$k_3/k_{-3}$=nucleotide incorporation (chemistry);
$k_4/k_{-4}$=polymerase isomerization (closed/open);
$k_5/k_{-5}$=polyphosphate release/binding;
$k_6/k_{-6}$=polymerase translocation.

Thus, during steps 104 through 110, the nucleotide is retained within the overall complex, and during steps 104 and 106, reversal of the reaction step will yield an unproductive event, i.e., not resulting in incorporation. For example, a bound nucleotide at step 104 may be released regardless of whether it is the correct nucleotide for incorporation.

By selecting the appropriate polymerase enzyme, polymerase reaction conditions, and polymerase substrates, the absolute and relative rates of the various steps can be controlled. We have found that by controlling the level and type of monovalent cation in the polymerization medium, the amount of time that during which nucleotide is associated with the enzyme prior to cleavage and release of polyphosphate can be controlled. These characteristics are particularly useful for sequencing applications, and in particular single-molecule DNA sequencing.

For the mechanism shown in FIG. 1, the time during which the nucleotide analog is associated with the enzyme prior to cleavage and release corresponds to the time after step 104 (nucleotide binding) and prior to step 112 (polyphosphate release).

In some cases, the steps during which the nucleotide analog is incorporated with the enzyme prior to cleavage of the polyphosphate constitutes a bright phase. In other cases, for example where quenching is used, the steps during which the nucleotide analog is incorporated with the enzyme constitutes a dark phase. As used herein, in either case this time period can be referred to as a pulse, and the length of time referred to as the pulse width.

An enzymatic process, such as nucleic acid polymerization, can have both slower, kinetically observable steps and faster steps which can be so fast that they have no measurable effect on the kinetics, or rate, of the reaction. In some reactions, there can be a single rate-limiting step. For such reactions, the kinetics can be characterized by the rate of that single step. Other reactions will not have a single rate-limiting step, but will have two or more steps which are close enough in rate such that the characteristics of each will contribute to the kinetics of the reaction. A kinetically observable step is generally a step which is slow enough relative to the other steps in the reaction such that it can be experimentally ascertained. The addition of monovalent cations as described herein appears to provide a way of lengthening one or more of the steps during the time the nucleotide analog is incorporated with the enzyme prior to cleavage and release of the polyphosphate while not lengthening the other steps of the process to the same extent. This allows for obtaining a significant change in the pulse width without a correspondingly large change in the interpulse distance.

Sequencing by Incorporation

For sequencing processes that rely upon monitoring of the incorporation of nucleotides into growing nascent strands being synthesized by the complex, the progress of the reaction through these steps is of significant importance. In particular, for certain "real-time" nucleotide incorporation monitoring processes, the detectability of the incorporation event is improved based upon the amount of time the nucleotide is incorporated into and retained within the synthesis complex during its ultimate incorporation into a primer extension product.

By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al., Science 299:682-686, January 2003, and Eid, J. et al., Science, 323(5910), 133-138 (2009), the full disclosures of which are incorporated herein by reference in their entirety for all purposes.

Figure 2:
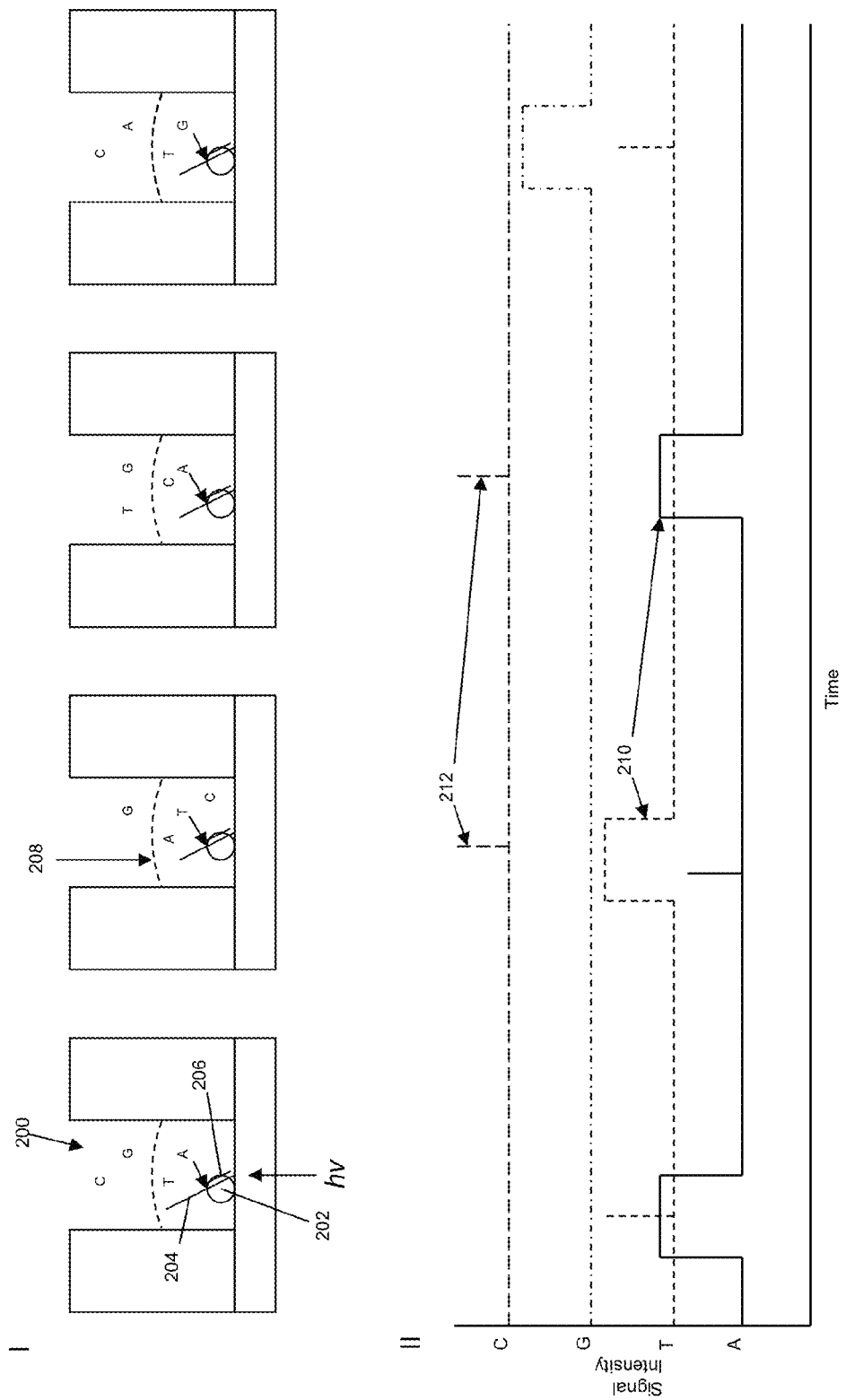
FIG. 2 schematically illustrates an exemplary single-molecule sequencing-by-incorporation process for which the compositions of the invention provide particular advantages.

In the first exemplary technique, as schematically illustrated in FIG. 2, a nucleic acid synthesis complex, including a polymerase enzyme 202, a template sequence 204 and a complementary primer sequence 206, is provided immobilized within an observation region 200, that permits illumination (as shown by hv) and observation of a small volume that includes the complex without excessive illumination of the surrounding volume (as illustrated by dashed line 208). By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume.

In particular, as shown in panel II of FIG. 2, when a nucleotide, e.g., A, is incorporated into by the polymerase, it is retained within the observation volume for a prolonged period of time, and upon continued illumination yields a prolonged fluorescent signal (shown by peak 210). By comparison, randomly diffusing and not incorporated nucleotides remain within the observation volume for much shorter periods of time, and thus produce only transient signals (such as peak 212), many of which go undetected, due to their extremely short duration.

In particularly preferred exemplary systems, the confined illumination volume is provided through the use of arrays of optically confined apertures termed zero-mode waveguides, e.g., as shown by confined reaction region 100 (ZMWs)(See, e.g., U.S. Pat. No. 6,917,726, which is incorporated herein by reference in its entirety for all purposes). For sequencing applications, the DNA polymerase is provided immobilized upon the bottom of the ZMW (See, e.g., Korlach et al., PNAS U.S.A. 105(4): 1176-1181. (2008), which is incorporated herein by reference in its entirety for all purposes.

In operation, the fluorescently labeled nucleotides (shown as A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuses away from the complex following incorporation of the associated nucleotide, nor do such labels interfere with the incorporation event. See, e.g., Korlach et al., Nucleosides, Nucleotides and Nucleic Acids, 27:1072:1083, 2008.

In the second exemplary technique, the nucleotides to be incorporated are each provided with interactive labeling components that are interactive with other labeling components provided coupled to, or sufficiently near the polymerase (which labels are interchangeably referred to herein as "complex borne"). Upon incorporation, the nucleotide borne labeling component is brought into sufficient proximity to the complex-borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair or FRET pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal, e.g., quenched or otherwise indicative of energy transfer. Upon incorporation and cleavage of the terminal phosphate groups, e.g., bearing a donor fluorophore, the quenching or other energy transfer is removed and the resulting characteristic fluorescent signal of the donor is observable.

In exploiting the foregoing processes, where the incorporation reaction occurs too rapidly, it may result in the incorporation event not being detected, i.e., the event speed exceeds the detection speed of the monitoring system. The missed detection of incorporated nucleotides can lead to an increased rate of errors in sequence determination, as omissions in the real sequence. In order to mitigate the potential for missed pulses due to short reaction times, in one aspect, the current invention can result in increased reaction time for incorporations. An advantage of the methods, systems, and compositions that control the time that the nucleotide analog is associated with the enzyme prior to phosphate release is an increased frequency of longer, detectable, binding/incorporation events. This advantage may also be seen as an increased ratio of longer, detectable pulses to shorter, non-detectable pulses, where the pulses represent binding/incorporation events.

Single-molecule sequencing often involves the optical observation of the polymerase process during the process of nucleotide incorporation, for example observation of the enzyme-DNA complex. During this process, there are generally two or more observable phases. For example, where a terminal-phosphate labeled nucleotide is used, and the enzyme-DNA complex is observed, there is a bright phase during the steps where the label is incorporated with (bound to) the polymerase enzyme, and a dark phase where there label is not incorporated with the enzyme. For the purposes of this invention, both the dark phase and the bright phase are generally referred to as observable phases, because the characteristics of these phases can be observed.

Whether a phase of the polymerase reaction is bright or dark can depend, for example, upon how and where the components of the reaction are labeled, and also how the reaction is observed. For example, as described above, the phase of the polymerase reaction where the nucleotide is bound can be bright where the nucleotide is labeled on its terminal phosphate. Alternatively, where there is a quenching dye associated with the enzyme or template, the bound state may be quenched, and therefore the phase where the nucleotide is bound can be a dark phase. Analogously, in a ZMW, or other optically confined configuration, the release and diffusion away of the label-bearing terminal phosphate may result in a dark phase, whereas in other systems, the release of the terminal phosphate may be observable, and therefore constitute a bright phase.

For example, consider again the reaction scheme of FIG. 1 in the context of the sequencing by incorporation embodiment described above which utilizes nucleotides having labels on their terminal phosphates. For this system, intermediates PDN, P*DN, P*D+1PPi, and PD+1PPi would all represent bright states of a bright phase because for each of these intermediates, the label is associated with the polymerase enzyme. In contrast, intermediates PD+1 and PD correspond to dark states of a dark phase, because for these intermediates, no dye is associated with the polymerase enzyme. In one aspect of the invention, any two of the steps which proceed from a bright intermediate, e.g. steps 106, 108, 110, and 112 of FIG. 1 are slow. By having two or more bright steps that are partially rate-limiting, the relative number of pulses with a longer pulse width, and/or detectable incorporation events increases.

Another example of a polymerase reaction with distinct observable phases is one in which the nucleotide is labeled such that its label does not dissociated from the enzyme upon product release, for example where the nucleotide is labeled on the base or on the sugar moiety. Here, the phase in which the label is associated with the active site of the enzyme (bright or dark) may extend past product release until translocation. For this example, an observable phase may extend from nucleotide binding until translocation.

In addition, the systems of the present invention may have two or more different distinct bright phases, for example, phases that can be distinguished based on different colors, e.g. different fluorescent emission wavelengths in the different observable phases. In some cases, the reactions observed as part of the present invention comprise two slow steps. Systems having two slow steps are described, for example, in U.S. Patent Application No. 2009/0286245 which is incorporated herein in its entirety for all purposes.

Polymerase Enzyme

One important aspect of obtaining a sequencing system having high accuracy is the selection of the enzyme that is used. Recombinant enzymes useful in the present invention are described, for example, in copending Published U.S. Patent Application 2010/0112645 "Generation of Modified Polymerases for Improved Accuracy in Single-molecule Sequencing", which is incorporated herein by reference for all purposes.

A modified polymerase (e.g., a modified recombinant Φ29-type DNA polymerase for example, a modified recombinant Φ29, B103, GA-1, PZA, Φ15, BS32, M2Y, Nf, G1, Cp-1, PRD1, PZE, SFS, Cp-5, Cp-7, PR4, PRS, PR722, or L17 polymerase) that exhibits one or more slow steps optionally includes a mutation (e.g., an amino acid substitution or insertion) at one or more of positions 484, 249, 179, 198, 211, 255, 259, 360, 363, 365, 370, 372, 378, 381, 383, 387, 389, 393, 433, 478, 480, 514, 251, 371, 379, 380, 383, 458, 486, 101, 188, 189, 303, 313, 395, 414, 497, 500, 531, 532, 534, 558, 570, 572, 574, 64, 305, 392, 402, 422, 496, 529, 538, 555, 575, 254, 390, 372-397, and 507-514, where numbering of positions is relative to wild-type Φ29 polymerase. Φ29-type DNA polymerases are homologous to the Φ29 DNA polymerase. For example, relative to wild-type Φ29 a modified recombinant polymerase can include at least one amino acid substitution or combination of substitutions selected from the group consisting of: an amino acid substitution at position 484; an amino acid substitution at position 198; an amino acid substitution at position 381; an amino acid substitution at position 387 and an amino acid substitution at position 484; an amino acid substitution at position 372, an amino acid substitution at position 480, and an amino acid substitution at position 484; an amino acid substitution at position 372, an amino acid substitution at position 387, and an amino acid substitution at position 480; an amino acid substitution at position 372, an amino acid substitution at position 387, and an amino acid substitution at position 484; an amino acid substitution at position 372, an amino acid substitution at position 387, an amino acid substitution at position 478, and an amino acid substitution at position 484; A484E; A484Y; N387L; T372Q; T372Y; T372Y and K478Y; K478Y; I370W; F198W; L381A; T368F; A484E, E375Y, K512Y, and T368F; A484Y, E375Y, K512Y, and T368F; N387L, E375Y, K512Y, and T368F; T372Q, E375Y, K512Y, and T368F; T372L, E375Y, K512Y, and T368F; T372Y, K478Y, E375Y, K512Y, and T368F; I370W, E375Y, K512Y, and T368F; F198W, E375Y, K512Y, and T368F; L381A, E375Y, K512Y, and T368F; and E375Y, K512Y, and T368F. A K512F substitution (or K512W, K512L, K512I, K512V, K512H, etc.) is optionally employed, e.g., where a K512Y substitution is listed herein. As another example, the modified polymerase can include an insertion of at least one amino acid (e.g., 1-7 amino acids, e.g., glycine) within residues 372-397 and/or 507-514. For example, a glycine residue can be introduced after residue 374, 375, 511, and/or 512 (designated as 374.1 G, 375.1 G, etc.). In some embodiments the enzyme has one or more of the amino acid substitutions E375Y, K512Y, T368F, A484E, A484Y, N387L, T372Q, T372L, K478Y, I370W, F198W, and L381A.

The polymerase mutations and mutational strategies noted herein can be combined with each other and with essentially any other available mutations and mutational strategies to confer additional improvements in, e.g., nucleotide analog specificity, enzyme processivity, improved retention time of labeled nucleotides in polymerase-DNA-nucleotide complexes, and the like. For example, the mutations and mutational strategies herein can be combined with those taught in, e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al. This combination of mutations/mutational strategies can be used to impart several simultaneous improvements to a polymerase (e.g., decreased branch fraction formation, improved specificity, improved processivity, altered rates, improved retention time, improved stability of the closed complex, etc.). In addition, polymerases can be further modified for application-specific reasons, such as to improve activity of the enzyme when bound to a surface, as taught, e.g., in WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al., or to include purification or handling tags as is taught in the cited references and as is common in the art.

Specific mutations noted herein can be used alone or in combination with each other and/or with available mutations as described in the references noted above, or can be used in polymerases that lack such previously described mutations. As just one example, essentially any mutation or combination thereof noted herein can be introduced into an E375Y/K512Y/T368F Φ29 polymerase, optionally, an exonuclease-deficient E375Y/K512Y/T368F Φ29 polymerase.

For example, enzymological approaches have been reported for enhancing the reaction kinetics of the polymerization reaction (See, e.g., published U.S. Patent Application Nos. 2007-0196846 and 2008-0108082, and Provisional Patent Application 61/094,843, the full disclosures of which are incorporated herein by reference in their entirety for all purposes), to increase the residence time of an incorporating nucleotide in the active site of a polymerase. While such reactions yield improvements in detectability of a bound nucleotide, and thus, an incorporation event, for a number of circumstances, it has been shown that increasing the retention time of a nucleotide complexed with a polymerase, also results in an increased likelihood that the nucleotide will be released unproductively.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Current Protocols in Molecular Biology, Ausubel et al., eds., Current Protocols, a joint venture between Greene Publishing Associates, Inc. and John Wiley & Sons, Inc., supplemented through 2004).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

For reference, the amino acid sequence of a wild-type Φ29 polymerase is presented below as SEQ ID NO:1.

enzyme, such as a single polymerase enzyme, and a small amount of primer template complex, such as a single primer-template complex associated with a single polymerase enzyme, and the second reaction has a higher concentration of polymerase enzyme, for example a concentration of polymerase enzyme of about 0.05 µM to 0.5 µM, and about 0.01 µM to about 0.1 µm.

Enzymatic reactions are often run in the presence of a buffer, which is used, in part, to control the pH of the reaction mixture. Buffers suitable for the invention include, for example, TAPS (3-{[tris(hydroxymethyl)methyl] amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the kinetics of the polymerase reaction, and can be used as one of the polymerase reaction conditions to obtain a sequencing reaction of the present invention. The pH can be adjusted to a value that produces a two slow-step reaction mechanism. The pH is generally between about 6 and about 9. In some cases, the pH is between about 6.5 and about 8.0. In some cases, the pH is between about 7.0 and 8.0. In some cases, the pH is about 6.5, 6.6, 6.7, 6.8, 6.9, 7.0, 7.1, 7.2, 7.3, 7.4, 7.5, 7.6,

```
SEQ ID  mkhmprkmys  cdfetttkve  dcrvwaygym  niedhseyki  gnsldefmaw
NO: 1   vlkvqadlyf  hnlkfdgafi  inwlerngfk  wsadglpnty  ntiisrmgqw ymidiclgyk  gkrkihtviy  dslkklpfpv  kkiakdfklt  vlkgdidyhk erpvgykitp  eeyayikndi  qiiaealliq  fkqgldrmta  gsdslkgfkd iittkkfkkv  fptlslgldk  evryayrggf  twlndrfkek  eigegmvfdv nslypaqmys  rllpygepiv  fegkyvwded  yplhiqhirc  efelkegyip tiqikrsrfy  kgneylkssg  geiadlwlsn  vdlelmkehy  dlynveyisg lkfkattglf  kdfidkwtyi  kttsegaikq  laklmlnsly  gkfasnpdvt gkvpylkeng  algfrlgeee  tkdpvytpmg  vfitawaryt  titaaqacyd riiycdtdsi  hltgteipdv  ikdivdpkkl  gywahestfk  rakylrqkty iqdiymkevd  gklvegspdd  ytdikfsvkc  agmtdkikke  vtfenfkvgf srkmkpkpvq  vpggvvlvdd  tftik
```

Polymerase Reaction Conditions

The polymerase reaction conditions can also be important for obtaining a sequencing system having high accuracy using the monovalent cations described herein. The polymerase reaction conditions include the type and concentration of buffer, the pH of the reaction, the temperature, the type and concentration of salts, the presence of particular additives which influence the kinetics of the enzyme, and the type, concentration, and relative amounts of various cofactors, including metal cofactors. The term "polymerase reaction conditions" as used herein generally excludes the concentration of the polymerase enzyme or the concentration of the primer-template complex. Thus, two reactions are run under substantially the same polymerase reaction conditions where the first reaction has a small amount of polymerase 7.7, 7.8, 7.9, or 8.0. In some cases, the pH that is used can affect the pulse widths. While pH can therefore be used to control pulse width to a certain extent, pH alone tends to be a difficult parameter to use to control pulse width because the pH can have a dramatic affect on other aspects of enzyme performance. Thus the use of monovalent cations such as alkali metals provides a valuable tool for asserting this type of control.

The temperature of the reaction can be adjusted to enhance the performance of the system. The reaction temperature may depend upon the type of polymerase which is employed. Temperatures between 15 OC and 90 OC, between 20 OC and 50 OC, between 20 OC and 40 OC, or between 20 OC and 30 OC can be used.

In some cases, additives can be added to the reaction mixture that will change the kinetics of the polymerase reaction in combination with the alkali metal cations of the invention. In some cases, the additives can interact with the active site of the enzyme, acting for example as competitive inhibitors. In some cases, additives can interact with portions of the enzyme away from the active site in a manner that will change the kinetics of the reaction so as to produce a reaction exhibiting two slow steps. Additives that can influence the kinetics include, for example, competitive, but otherwise unreactive substrates or inhibitors in analytical reactions to modulate the rate of reaction as described in copending U.S. Utility patent application Ser. No. 12/370,472 the full disclosures of which is incorporated herein by reference in its entirety for all purposes.

Additives include organic solvents. The solvent additives are generally water soluble organic solvents. The solvents need not be soluble at all concentrations, but are generally soluble at the amounts used to control the kinetics of the polymerase reaction. While not being bound by theory, it is believed that the solvents can influence the three dimensional conformation of the polymerase enzyme which can affect the rates of the various steps in the polymerase reaction. For example, the solvents can provide affect steps involving conformational changes such as the isomerization steps shown in FIG. 1. Added solvents can also affect, and in some cases slow, the translocation step. The slowing of the translocation step can increase interpulse distances, and can be used in conjunction with slowing the nucleotide binding step, for example, to obtain two slow steps in the steps in which the nucleotide is not associated with the enzyme, for instance resulting in two slow steps in the dark phase of a polymerase reaction. In some cases, the solvent additives can increase the interpulse distance without substantially affecting the pulse widths in single-molecule sequencing. In some cases, the solvents act by influencing hydrogen bonding interactions. In some case, the addition of solvent can be used to change the rate of one or more steps in the polymerase reaction. The addition of organic solvents can be used, for example to increase the mean time between pulses (interpulse distance).

The water miscible organic solvents that can be used to control the rates of one or more steps of the polymerase reaction in single-molecule sequencing include alcohols, amines, amides, nitriles, sulfoxides, ethers, and esters and small molecules having more than one of these functional groups. Exemplary solvents include alcohols such as methanol, ethanol, propanol, isopropanol, glycerol, and small alcohols. The alcohols can have one, two, three, or more alcohol groups. Exemplary solvents include small molecule ethers such as tetrahydrofuran (THF), and dioxane. In some embodiments the solvent is dimethylacetamide (DMA). In some embodiments the solvent is dimethylsulfoxide (DMSO). In some embodiments, the solvent is dimethylformamide (DMF). In some embodiments the solvent is acetonitrile. In some embodiments the solvent is formyl morpholinse (FMP).

The water miscible organic solvent can be present in any amount sufficient to control the kinetics of the polymerase reaction. The solvents are generally added in an amount less than 40% of the solvent weight by weight or volume by volume. In some embodiments the solvents are added between about 0.1% and 30%, between about 1% and about 20%, between about 2% and about 15%, and between about 5% and 12%. The effective amount for controlling the kinetics can be determined by the methods described herein and those known in the art.

A suitable additive for obtaining a two slow-step system is the amino acid, cysteine, having the chemical formula HO2CCH(NH2)CH2SH. Cysteine can be added to the reaction mixture as a salt, for example, as the hydrochloride salt. Generally, the naturally occurring L-cysteine (Cys) is used. Other additives with chemical structures related to cysteine can also be used. For example, homocysteine or any other suitable natural or artificial amino acid having an S atom, and in particular, a thiol group. We have found that the addition of cysteine can lead to an increase in both overall yield and in accuracy of single molecule sequencing. While not being bound by theory, Cys, because of its thiol side chain and AA polar moiety may have beneficial effects on both polymerase and nucleotides during sequencing. An increase in the pulse width with the addition of Cys has also been observed. The effect could be different from or cumulative to that of dithiothreitol (DTT), which can also be added to the sequencing reaction, owing to only a single —SH functionality in Cys and, therefore, larger tendency to participate in intermolecular interactions. In addition, Cys may influence the analog binding to polymerase via linking the two with hydrogen and S—S bonds. Cysteine can be added at any level suitable for improving the properties of the enzymatic reaction. For example, cysteine can be added at amounts greater than about 0.1 mM, greater than about 0.5 mM, greater than about 1 mM, greater than about 5 mM, greater than about 10 mM. In some cases, the cysteine can be added in amounts less than about 200 mM, less than about 100 mM, less than about 50 mM, less than about 20 mM, or less than about 10 mM. In some cases, the cysteine is present in amounts between about 1 mM and about 100 mM, between about 5 mM and about 50 mM, or between about 10 mM and about 30 mm.

Additives such as dithiothreitol (DTT), can also be present in the reaction. In some cases, such additives, which are often used in enzymatic systems, do not directly lead to two slow-step systems, but are useful for the functioning of the enzyme during, for example, nucleic acid synthesis.

One aspect of controlling the polymerase reaction conditions relates to the selection of the type, level, and relative amounts of cofactors. For example, during the course of the polymerase reaction, divalent metal co-factors, such as magnesium or manganese, will interact with the enzyme-substrate complex, playing a structural role in the definition of the active site. For a discussion of metal co-factor interaction in polymerase reactions, see, e.g., Arndt, et al., Biochemistry (2001) 40:5368-5375.

For example, and without being bound to any particular theory of operation, it is understood that metal cofactor binding in and around the active site serves to stabilize binding of incoming nucleotides and is required for subsequent catalysis, e.g., as shown in steps 106 and 108. Other metal cofactor binding sites in polymerases, e.g., in the exonuclease domains, are understood to contribute to different functionality of the overall proteins, such as exonuclease activity.

In the context of the present invention, however, it has been discovered that modulation, and particularly competitive modulation of divalent metal cofactors to the synthesis reaction can provide substantial benefits in terms of reaction kinetics without a consequent increase in negative reaction events.

In the synthesis reaction, certain divalent metal cofactors, such as magnesium and manganese or trivalent metal cofactors are known to interact with the polymerase to modulate the progress of the reaction (See, e.g., U.S. Pat. No. 5,409,811). Other divalent metal ions, such as $Ca^{2+}$, have been shown to interact with the polymerase, such as phi29 derived polymerases, to negative effect, e.g., to halt polymerization.

As will be appreciated, depending upon the nature of the polymerization reaction, environmental conditions, the polymerase used, the nucleotides employed, etc., different metal co-factors will have widely varying catalytic effects upon the polymerization reaction. In the context of the present invention, different metal co-factors will be referred to herein based upon their relative catalytic impact on the polymerization reaction, as compared to a different metal included under the same reaction conditions. For purposes of discussion, a first metal co-factor that interacts with the polymerase complex to support the polymerization reaction to a higher level than a second metal co-factor under the same conditions is termed a "catalytic metal ion" or "catalytic metal". In preferred aspects, such catalytic metals support the continued, iterative or processive polymerization of nucleic acids under the particular polymerase reaction conditions, e.g., through the addition on multiple bases, while in some cases, a given type of metal cofactor may only support addition of a single base. Such metals may be sufficiently catalytic, depending upon the specific application.

In certain cases, particularly preferred divalent metal ions or catalytic metals, include, e.g., $Mn^{2+}$, and in some cases will include $Mg^{2+}$. Less preferred multivalent metal ions that may provide a sufficient level of catalytic activity depending upon the desired application include, e.g., zinc.

For purposes of the invention, metal ions that interact with the polymerase, but that do not promote the polymerization reaction, and in many cases act to arrest or prevent polymerization, are termed "non-catalytic metals". Included among the non-catalytic metals for various polymerase systems are calcium, barium, strontium, iron, cobalt, nickel, tin, zinc, and europium. For example, these metals can be added to the polymerization reaction in salt form such as $Sr(OAc)_2$, $Sr(OAc)_2$, $CoCl_2$, $SnCl_2$, $CaCl_2$, or $ZnSO_4$. As will be appreciated, a first metal co-factor that might be deemed to be catalytic under a first set of reaction conditions or relative to second metal co-factor, may be deemed to be a non-catalytic metal under another different set of reaction conditions, or with respect to a third metal co-factor. By way of example, as noted previously, magnesium is generally known to support DNA polymerization. However, under certain conditions, and/or relative to manganese, magnesium can operate as a non-catalytic co-factor. For purposes of the present invention, a catalytic co-factor will support polymerization to a greater degree than the non-catalytic metal under the same reaction conditions. The relative catalytic impact will typically be a function of the reactant turnover rate of the polymerization complex, with catalytic metal co-factors promoting a turnover that is at least 2×, more preferably at least 5×, still more preferably, at least 10×, and in some cases 20×, 50× or more than that of the non-catalytic metal co-factor under the same reaction conditions. Accordingly, in the context of various aspects of the invention, the polymerization complex is exposed to two different co-factors that have substantially different impacts on the polymerization reaction under the given set of reaction conditions, where the first metal co-factor promotes polymerization to a substantially greater degree than the second metal co-factor, or restated in the negative context, the second metal co-factor arrests or halts polymerization to a substantially greater degree than the first.

Although generally described in terms of mixtures of a first and second metal co-factors, where the first has higher catalytic impact than the second, it will be appreciated that the reaction mixtures may include more than two metal co-factors of differing catalytic impact upon the polymerization complex. For example, the reaction mixtures may include three, four, five or more different metal co-factors that have differing catalytic impacts, i.e., promotion or inhibition of polymerization reaction under the given reaction conditions. Thus, in its broadest sense, the invention includes polymerization reaction mixtures that include mixtures of different metal co-factors that interact with the polymerization complex, where the different metal co-factors have different catalytic impacts upon the polymerization reaction, e.g., different effects on enzyme turnover rates, relative to each other. Such reaction mixtures can include two, three, four, five or more different metal co-factors that are capable of interacting with the polymerization complex, and particularly the polymerase itself, to promote or inhibit the polymerization reaction, relative to one or more other metal co-factors that are present.

The reactions of the invention can be carried out using particular ratios of catalytic and non-catalytic metals. The molar ratio of catalytic to non-catalytic metals in the reaction mixture will generally vary depending upon the type of kinetic modulation desired for a given synthesis reaction, where slower incorporation would suggest higher levels of non-catalytic metal ions. Typically, such ratios of catalytic to non-catalytic metals in the reaction mixture will vary from about 10:1 to about 1:10, and preferably, from about 10:1 to about 1:5, depending upon the desired level of modulation, the particular enzyme system employed, the catalytic and non-catalytic metal cofactors that are used, and the reaction conditions. In particularly preferred aspects, the ratios of catalytic to non-catalytic metals will be in the range of from about 5:1 to about 1:1, with ratios of from about 2.5:1 to about 1.5:1 being particularly preferred.

In addition to the presence of such metals at the ratios described herein, the absolute concentration of such metals in the reaction mixtures will typically range from about 0.05 mM to about 50 mM, in some cases from about 0.1 mM to about 10 mM, in some cases from about 0.1 mM to about 5 mM. The composition can include, for example, from about 0.1 mM $MnCl_2$ to about 1 mM $MnCl_2$ and from about 0.1 mM $CaCl_2$ to about 2 mM $CaCl_2$; or from about 0.2 mM $MnCl_2$ to about 1 mM $MnCl_2$ and from about 0.4 mM $CaCl_2$ to about 1.5 mM $CaCl_2$.

Systems having mixed catalytic/non-catalytic metals are described in more detail in Published U.S. Patent Application No. 2009/0286245, the full disclosure of which is incorporated by reference herein for all purposes.

Polymerase Reaction Substrates

The polymerase reactions of the invention include polymerase reaction substrates. The substrates that are selected can be selected to influence the kinetics of the polymerase reaction, and can be utilized to prepare a polymerase reaction system for sequencing using the monovalent cations of the invention. The polymerase reaction substrates include the template nucleic acid, a primer, and one or more nucleotides. The template nucleic acid is the molecule for which the complimentary sequence is synthesized in the polymerase reaction. In some cases, the template nucleic acid is linear, in some cases, the template nucleic acid is circular. The template nucleic acid can be DNA, RNA, or can be a non-natural RNA analog or DNA analog. Any template nucleic acid that is suitable for replication by a polymerase enzyme can be used herein.

By "nucleic acid" or "oligonucleotide" or grammatical equivalents herein means at least two nucleotides covalently linked together. A nucleic acid of the present invention will generally contain phosphodiester bonds, although in some cases, nucleic acid analogs are included that may have alternate backbones, comprising, for example, phosphoramide, phosphorothioate, phosphorodithioate, and peptide nucleic acid backbones and linkages. Other analog nucleic acids include those with positive backbones; non-ionic backbones, and non-ribose backbones, including those described in U.S. Pat. Nos. 5,235,033 and 5,034,506. The template nucleic acid may also have other modifications, such as the inclusion of heteroatoms, the attachment of labels, such as dyes, or substitution with functional groups which will still allow for base pairing and for recognition by the enzyme.

The synthesis reaction will typically include a template or target nucleic acid sequence that is sought to be replicated, as well as a primer sequence that specifically hybridizes to a portion of the template or target sequence.

The template sequence may be provided in any of a number of different format types depending upon the desired application. For example, in some cases, the template sequence may be a linear single or double stranded nucleic acid sequence. In still other embodiments, the template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220674, filed Jul. 25, 2008. Alternate functional circular constructs are also described in U.S. Patent Application [unassigned], entitled "Method and Compositions for Nucleic Acid Sample Preparation" filed Mar. 27, 2009, and U.S. patent application Ser. No. 12/413,258, the full disclosures of each of which are incorporated herein by reference in their entirety for all purposes.

Briefly, such alternate constructs include template sequences that possess a central double stranded portion that is linked at each end by an appropriate linking oligonucleotide, such as a hairpin loop segment. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

The polymerase enzymes of the invention generally require a primer, which is usually a short oligonucleotide that is complementary to a portion of the template nucleic acid. The primers of the invention can comprise naturally occurring RNA or DNA oligonucleotides. The primers of the invention may also be synthetic analogs. The primers may have alternative backbones as described above for the nucleic acids of the invention. The primer may also have other modifications, such as the inclusion of heteroatoms, the attachment of labels, such as dyes, or substitution with functional groups which will still allow for base pairing and for recognition by the enzyme. Primers can select tighter binding primer sequences, e.g., GC rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template.

As used in the art, the term nucleotide refers both to the nucleoside triphosphates that are added to a growing nucleic acid chain in the polymerase reaction, and also to refer to the individual units of a nucleic acid molecule, for example the units of DNA and RNA. Herein, the term nucleotide used in consistent with its use in the art. Whether the term nucleotide refers to the substrate molecule to be added to the growing nucleic acid or to the units in the nucleic acid chain can be derived from the context in which the term used.

The nucleotides or set of nucleotides of the invention can be naturally occurring nucleotides or modified nucleotides (nucleotide analogs). The nucleotides used in the invention, whether natural, unnatural, modified or analog are suitable for participation in the polymerase reaction. For example, the term nucleotide is used to refer to nucleotides that are labeled with fluorescent dye group. The term nucleotide may also be used to refer to nucleotides having other than three phosphate groups, for example 4, 5, 6, 7 or more phosphate groups. Such nucleotides have been described, for example in U.S. Pat. Nos. 6,936,702 and 7,041,812. Labels such as fluorescent dye group may be located in various positions on the nucleotide. In some cases, a fluorescent dye is located on the terminal phosphate of the nucleotide. The term nucleotide as used herein also comprises nucleotide analogs.

The nucleotide compositions may include nucleoside triphosphates, or analogs of such compounds. For example, in some cases, the reaction mixtures will include nucleotide analogs having longer phosphate chains, such as nucleoside tetra-, penta-, hexa- or even heptaphosphates. In addition, the nucleotide analogs of the compositions of the invention may additionally include other components, such as detectable labeling groups. Such detectable labeling groups will typically impart an optically or electrochemically detectable property to the nucleotide analogs being incorporated into the synthesis reaction. In particularly preferred aspects, fluorescent labeling groups, i.e., labeling groups that emit light of one wavelength when excited with light of another wavelength, are used as the labeling groups. For purposes of the present disclosure, the foregoing or later discussed nucleotide or nucleotide analog compositions whether labeled or unlabeled, possessing of three or more phosphate groups, or otherwise modified, are generally referred to herein as nucleotides.

Typically, each of the different types of nucleotide analogs will be labeled with a detectably different fluorescent labeling group, e.g., that possesses a detectably distinct fluorescent emission and/or excitation spectrum, such that it may be identified and distinguished from different nucleotides upon incorporation. For example, each of the different types of nucleotides, e.g., A, T, G and C, will be labeled with a fluorophore having a different emission spectrum. For certain embodiments, the nucleotide may include a fluorescent labeling group coupled to a portion of the nucleotide that is incorporated into the nascent nucleic acid strand being produced during synthesis, e.g., the nucleobase or sugar moiety. Nucleotide compositions having fluorophores coupled to these portions have been previously described (See, e.g., U.S. Pat. No. 5,476,928 and 4,711,955 to Ward et al.). As a result of the label group being coupled to the base or sugar portion of the nucleotide, upon incorporation, the nascent strand will include the labeling group. This labeling group may then remain or be removed, e.g., through the use of cleavable linkages joining the label to the nucleotide (See, e.g., U.S. Pat. No. 7,057,026). A variety of different fluorophore types, including both organic and inorganic fluorescent materials, have been described for biological applications and are likewise applicable in the instant invention.

Alternatively and preferably, the labeling group is coupled to a portion of the polyphosphate chain that is removed by the polymerase action during the incorporation event, e.g., the beta, gamma or further distal phosphate group. Examples of such phosphate labeled nucleotide analogs and their use in sequencing applications are described in, e.g., U.S. Pat. Nos. 6,399,335, 6,762,048, 7,041,812 and published U.S. Patent Application No. 2006-0063173. Because the label is included on a portion of the nucleotide that is cleaved during incorporation, the labeling group is not actually incorporated into the nascent strand, but instead, diffuses away from the synthesis complex. As described previously, where the complex is provided within an optical confinement, e.g., a zero-mode waveguide, the act of incorporation provides a characteristic retention of the label prior to its cleavage and diffusion away, so as to permit the recognition of an incorporation event. Further, by identifying the spectral characteristics of the label associated with the base being incorporated, one can identify the specific type of base.

In certain embodiments, the nucleotides or the complex as a whole may be provided with cooperative fluorescent labeling groups, e.g., that act cooperatively as a donor-quencher or fluorescent resonant energy transfer pair, to provide labeling. As noted above, in this context, the necessity for optical confinement to eliminate background signal from unincorporated labels or nucleotides is reduced, as substantially only interacting labels brought into sufficient proximity by the incorporation event (in the case of complex and nucleotide bound interactive labels), or only labels separated by cleavage of the polyphosphate chain upon incorporation, will produce a characteristic signal indicative of incorporation.

Other fluorescent labeling groups may likewise be employed in the nucleotide compositions, including inorganic fluorescent materials, such as semiconductor nanocrystals, like II-VI or III-V semiconductor nanocrystals, including CdSe, CdTe, InS, ZnS or other nanocrystal compositions, available from, e.g., e-Biosciences, Inc. (San Diego, Calif.), and Life Technologies, Inc.

In preferred aspects, the labeling groups incorporated into the analogs of the invention comprise optically detectable moieties, including luminescent, chemiluminescent, fluorescent, fluorogenic, chromophoric and/or chromogenic moieties, with fluorescent and/or fluorogenic labels being particularly preferred. A variety of different label moieties are readily employed in nucleotide analogs, and particularly, the compound of the invention. Such groups include fluorescein labels, rhodamine labels, cyanine labels (i.e., Cy3, Cy5, and the like, generally available from the Amersham Biosciences division of GE Healthcare), the Alexa family of fluorescent dyes and other fluorescent and fluorogenic dyes available from Molecular Probes/Invitrogen, Inc., and described in 'The Handbook—A Guide to Fluorescent Probes and Labeling Technologies, Tenth Edition' (2005) (available from Invitrogen, Inc./Molecular Probes). A variety of other fluorescent and fluorogenic labels for use with nucleoside polyphosphates, and which would be applicable to the compounds of the present invention are described in, e.g., Published U.S. Patent Application No. 2003/0124576, the full disclosure of which is incorporated herein in its entirety for all purposes.

The label group may be directly coupled to the terminal phosphorus atom of the analog structure, in alternative aspects, it may additionally include a linker molecule to provide the coupling through, e.g., an alkylphosphonate linkage. A wide variety of linkers and linker chemistries are known in the art of synthetic chemistry may be employed in coupling the labeling group to the analogs of the invention. For example, such linkers may include organic linkers such as alkane or alkene linkers of from about C2 to about C20, or longer, polyethyleneglycol (PEG) linkers, aryl, heterocyclic, saturated or unsaturated aliphatic structures comprised of single or connected rings, amino acid linkers, peptide linkers, nucleic acid linkers, PNA, LNAs, or the like or phosphate or phosphonate group containing linkers. In preferred aspects, alkyl, e.g., alkane, alkene, alkyne alkoxy or alkenyl, or ethylene glycol linkers are used. Some examples of linkers are described in Published U.S. Patent Application No. 2004/0241716, which is incorporated herein by reference in its entirety for all purposes. Additionally, such linkers may be selectively cleavable linkers, e.g., photo- or chemically cleavable linkers or the like. The linkers can be alkyl, aryl, or ester linkers. The linkers can be, amino-alkyl linkers, e.g., amino-hexyl linkers. In some cases, the linkers can be rigid linkers such as disclosed in U.S. patent application Ser. No. 12/403,090.

Single-Molecule Sequencing Processes and Systems

As noted, the amount and type of monovalent cation can be used to control the pulse width related to nucleotide interaction with a polymerase enzyme as part of a synthesis complex. Accordingly, in particularly preferred aspects, the synthesis complexes in such reaction mixtures are arrayed so as to permit observation of the individual complexes that are being so modulated. In arraying individual complexes to be individually optically resolvable, the systems of the invention will position the complexes on solid supports such that there is sufficient distance between adjacent individual complexes as to allow optical signals from such adjacent complexes to be optically distinguishable from each other.

Typically, such complexes will be provided with at least 50 nm and more preferably at least 100 nm of distance between adjacent complexes, in order to permit optical signals, and particularly fluorescent signals, to be individually resolvable. Examples of arrays of individually resolvable molecules are described in, e.g., U.S. Pat. No. 6,787,308.

In some cases, individual complexes may be provided within separate discrete regions of a support. For example, in some cases, individual complexes may be provided within individual optical confinement structures, such as zero-mode waveguide cores. Examples of such waveguides and processes for immobilizing individual complexes therein are described in, e.g., Published International Patent Application No. WO 2007/123763, the full disclosure of which is incorporated herein by reference in its entirety for all purposes.

As noted previously, in preferred aspects, the synthesis complexes are provided immobilized upon solid supports, and preferably, upon supporting substrates. The complexes may be coupled to the solid supports through one or more of the different groups that make up the complex. For example, in the case of nucleic acid polymerization complexes, attachment to the solid support may be through an attachment with one or more of the polymerase enzyme, the primer sequence and/or the template sequence in the complex. Further, the attachment may comprise a covalent attachment to the solid support or it may comprise a non-covalent association. For example, in particularly preferred aspects, affinity based associations between the support and the complex are envisioned. Such affinity associations include, for example, avidin/streptavidin/neutravidin associations with biotin or biotinylated groups, antibody/antigen associations, GST/glutathione interactions, nucleic acid hybridization interactions, and the like. In particularly preferred aspects, the complex is attached to the solid support through the provision of an avidin group, e.g., streptavidin, on the support, which specifically interacts with a biotin group that is coupled to the polymerase enzyme.

Methods of providing binding groups on the substrate surface that result in the immobilization of optically resolvable complexes are described in, e.g., published U.S. Patent Application No. 2007-0077564, incorporated herein by reference in its entirety for all purposes, and WO 2007123763, previously incorporated herein by reference.

The sequencing processes, e.g., using the substrates described above and the synthesis compositions of the invention, are generally exploited in the context of a fluorescence microscope system that is capable of illuminating the various complexes on the substrate, and obtaining detecting and separately recording fluorescent signals from these complexes. Such systems typically employ one or more illumination sources that provide excitation light of appropriate wavelength(s) for the labels being used. An optical train directs the excitation light at the reaction region(s) and collects emitted fluorescent signals and directs them to an appropriate detector or detectors. Additional components of the optical train can provide for separation of spectrally different signals, e.g., from different fluorescent labels, and direction of these separated signals to different portions of a single detector or to different detectors. Other components may provide for spatial filtering of optical signals, focusing and direction of the excitation and or emission light to and from the substrate.

Figure 3:
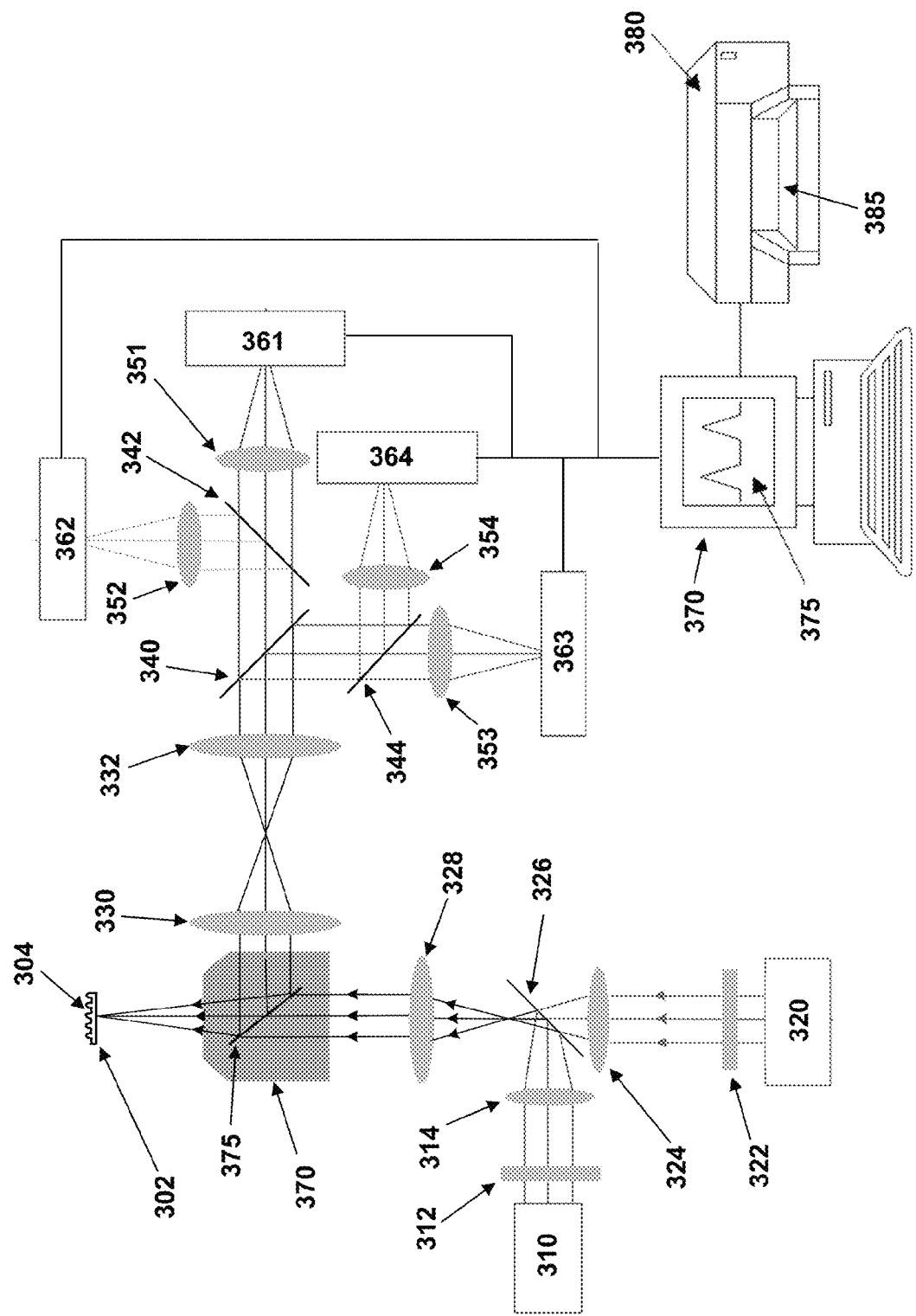
FIG. 3 schematically illustrates a simplified system for analysis of sequencing-by-incorporation reactions.

One such exemplary system is shown in FIG. 3. An exemplary system is also described in Lundquist et al., Published U.S. Patent Application No. 2007-0036511, Optics Letters, Vol. 33, Issue 9, pp. 1026-1028, the full disclosure of which is incorporated herein by reference in its entirety for all purposes.

Fluorescence reflective optical trains can be used in the applications of the systems of the invention. For a discussion on the advantages of such systems, see, e.g., U.S. patent application Ser. No. 11/704,689, filed Feb. 9, 2007, Ser. No. 11/483,413, filed Jul. 7, 2006, and Ser. No. 11/704,733, filed Feb. 9, 2007, the full disclosures of which are incorporated herein by reference in their entirety for all purpose.

For purposes of the present invention, the processes and systems will be described with reference to detection of incorporation events in a real time, sequence by incorporation process, e.g., as described in U.S. Pat. Nos. 7,056,661, 7,052,847, 7,033,764 and 7,056,676 (the full disclosures of which are incorporated herein by reference in their entirety for all purposes), when carried out in arrays of discrete reaction regions or locations. An exemplary sequencing system for use in conjunction with the invention is shown in FIG. 3. As shown, the system includes a substrate 302 that includes a plurality of discrete sources of optical signals, e.g., reaction wells, apertures, or optical confinements or reaction locations 304. In typical systems, reaction locations 304 are regularly spaced and thus substrate 302 can also be understood as an array 302 of reaction locations 304. The array 302 can comprise a transparent substrate having cladding layer on its top surface with an array of nanoscale apertures extending through the cladding to the transparent substrate. This configuration allows for one or more samples to be added to the top surface of the array, and for the array to be observed through the transparent substrate from below, such that only the light from the apertures is observed. The array can be illuminated from below as shown in FIG. 3, and in some embodiments, the array can also be illuminated from above (not shown in FIG. 3).

For illumination from below, one or more excitation light sources, e.g., lasers 310 and 320, are provided in the system and positioned to direct excitation radiation at the various signal sources. Here, two lasers are used in order to provide different excitation wavelengths, for example with one laser 310 providing illumination in the red, and laser 320 providing illumination in the green. The use of multiple laser excitation sources allows for the optimal excitation of multiple labels in a sample in contact with the array. The excitation illumination can be a flood illumination, or can be directed to discrete regions on the array, for example, by breaking the excitation beam into an array of beamlets, each beamlet directed to a feature on the array. In order to break the excitations beams into an array of beamlets, a diffractive optical element (DOE). In the system of FIG. 3, the light from excitation sources 310 and 320 is sent through DOE components 312 and 322 respectively. The use of a DOE for providing an array of beamlets is provided, e.g. in U.S. Pat. No. 7,714,303, which is incorporated by reference herein in its entirety. Excitation light is then passed through illumination relay lenses 314 and 324 to interact with dichroic 326. In the system of FIG. 3, the red light from laser 310 is reflected off of dichroic 326, and the green light from laser 320 is directed through the dichroic 326. The excitation light is then passed through illumination tube lens 328 into objective lens 370 and onto the array 302.

Emitted signals from sources 304 are then collected by the optical components, e.g., objective 370, comprising dichroic element 375 which allows the illumination light to pass through and reflects the excitation light. The emitted light passes through collection tube lens 330 and collection relay lens 332. The emitted light is then separated into D different spectral channels, and each spectral channel is directed to a different detector. In the system of FIG. 3, the light is separated into four different channels, each channel corresponding predominantly to one of four labels to be detected in the sample. Thus, the system allows the user to obtain four two dimensional images, each image corresponding to one of the four labels. In order to separate the light into the four spectral channels, dichroics 340, 342, and 344 are used. Dichroic 340 allows the light for channels 1 and 2 to pass while reflecting the light for channels 3 and 4. Dichroic 342 allows the light for channel 1 to pass, through collection imaging lens 351 to detector 361, and reflects the light for channel 2 through collection imaging lens 352 to detector 362. Dichroic 344 allows the light for channel 3 to pass, through collection imaging lens 353 onto detector 363, and reflects the light for channel 4 through collection illumination lens 354 onto detector 364. Each of the detectors 361-364 comprise arrays of pixels. The detectors can be, for example, CMOS, EMCCD, or CCD arrays. Each of the detectors obtains 2-dimensional images of the channel that is directed to that detector. The data from those signals is transmitted to an appropriate data processing unit, e.g., computer 370, where the data is subjected to processing, interpretation, and analysis. The data processing unit is configured to process the data both pixel by pixel and pixel region by pixel region, where each pixel region corresponds to a feature on the substrate. The data processing unit can receive data from calibration runs in order to define software mask pixel weighting, spectral weighting, and noise parameters. These parameters and weightings can be applied to signals that are measured on the detectors during an analytical reaction such as during sequencing. In some embodiments, the data processing unit is configured to define and apply software mask pixel weighting, spectral weighting, and noise parameters that are determined and then applied during an analytical reaction such as during sequencing.

Analyzed and processed obtained from the analytical reactions can ultimately be presented in a user ready format, e.g., on display 375, printout 385 from printer 380, or the like, or may be stored in an appropriate database, transmitted to another computer system, or recorded onto tangible media for further analysis and/or later review. Connection of the detector to the computer may take on a variety of different forms. For example, in preferred aspects, the detector is coupled to appropriate Analog to Digital (A/D) converter that is then coupled to an appropriate connector in the computer. Such connections may be standard USB connections, Firewire® connections, Ethernet connections or other high speed data connections. In other cases, the detector or camera may be formatted to provide output in a digital format and be readily connected to the computer without any intermediate components.

This system, and other hardware descriptions herein, are provided solely as a specific example of sample handling and image capture hardware to provide a better understanding of the invention. It should be understood, however, that the present invention is directed to data analysis and interpretation of a wide variety of real-time florescent detecting systems, including systems that use substantially different illumination optics, systems that include different detector elements (e.g., EB-CMOS detectors, CCD's, etc.), and/or systems that localize a template sequence other than using the zero mode wave-guides described herein.

In the context of the nucleic acid sequencing methods described herein, it will be appreciated that the signal sources each represent sequencing reactions, and particularly, polymerase mediated, template dependent primer extension reactions, where in preferred aspects, each base incorporation event results in a prolonged illumination (or localization) of one of four differentially labeled nucleotides being incorporated, so as to yield a recognizable pulse that carries a distinguishable spectral profile or color.

The present invention can include computer implemented processes, and/or software incorporated onto a computer readable medium instructing such processes, as set forth in greater detail below. As such, signal data generated by the reactions and optical systems described above, is input or otherwise received into a computer or other data processor, and subjected to one or more of the various process steps or components set forth below. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or MacIntosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

While described in terms of a particular sequencing by incorporation process or system, it will be appreciated that certain aspects of the processes of the invention may be applied to a broader range of analytical reactions or other operations and varying system configurations than those described for exemplary purposes.

In certain embodiments, the sequencing compositions described herein will be provided in whole, or in part, in kit form enabling one to carry out the processes described herein. Such kits will typically comprise one or more components of the reaction complex, such as the polymerase enzyme and primer sequences. Such kits will also typically include buffers and reagents that provide the catalytic and non-catalytic metal co-factors employed in the processes described herein. The kits will also optionally include other components for carrying out sequencing applications in accordance with those methods described herein. In particular, such kits may include ZMW array substrates for use in observing individual reaction complexes as described herein.

In addition to the various components set forth above, the kits will typically include instructions for combining the various components in the amounts and/or ratios set forth herein, to carry out the desired processes, as also described or referenced herein, e.g., for performing sequence by incorporation reactions.

EXAMPLE

Example 1

Single-Molecule Sequencing in Zero-Mode Waveguides with Li+

Sequencing reactions are carried out in a zero-mode waveguide array having 3000 discrete cores. The reactions are observed using a highly multiplexed confocal fluorescent microscope providing a targeted illumination profile, e.g., a separate spot for each core (See, e.g., U.S. patent application Ser. No. 12/151,979, filed May 9, 2008, and incorporated herein by reference in its entirety for all purposes). Fluorescent signals from the various ZMWs are detected on an EMCCD camera for 5-7 minutes, and are subjected to pulse recognition and base calling processes (See, e.g., Published U.S. Patent Application No. 2009-0024331, and incorporated herein by reference in its entirety for all purposes). The sequencing was carried out as described in Eid, J. et al., Science, 323(5910), 133-138 (2009) and corresponding supplemental information.

For each of the sequencing reactions the laser power was 1.25 $\mu W/\mu m^2$ and a camera frame rate of 100 FPS. The template was a circular vD "SMRTbe11" template of about 1000 kb as described in U.S. patent application Ser. No.12/383,855 filed Mar. 27, 2009. The polymerase enzyme immobilized in the zero mode waveguide was a mutant $\Phi 29$ polymerase as described in U.S. patent application Ser. No. 12/384,122 filed Mar. 30, 2009. The reaction mixture had a TRIS pH 8.0 buffer, antioxidants, 120 mM DTT, 120 mM KOAc to control ionic strength; 30 mM MgOAc and 4% organic solvent additive. The mixture also contained a set of nucleotide analogs corresponding to A, G, C, and T, each present at 500 nM, each having a polyphosphate chain with 6 phosphates with a unique fluorescent dye attached to the terminal phosphate. 30 minute movies of the sequencing reactions were obtained. Data was collected on the pulse width, the interpulse distance (IPD), read length, z-score, and accuracy. Li+ was added as an acetate salt.

Figure 4:
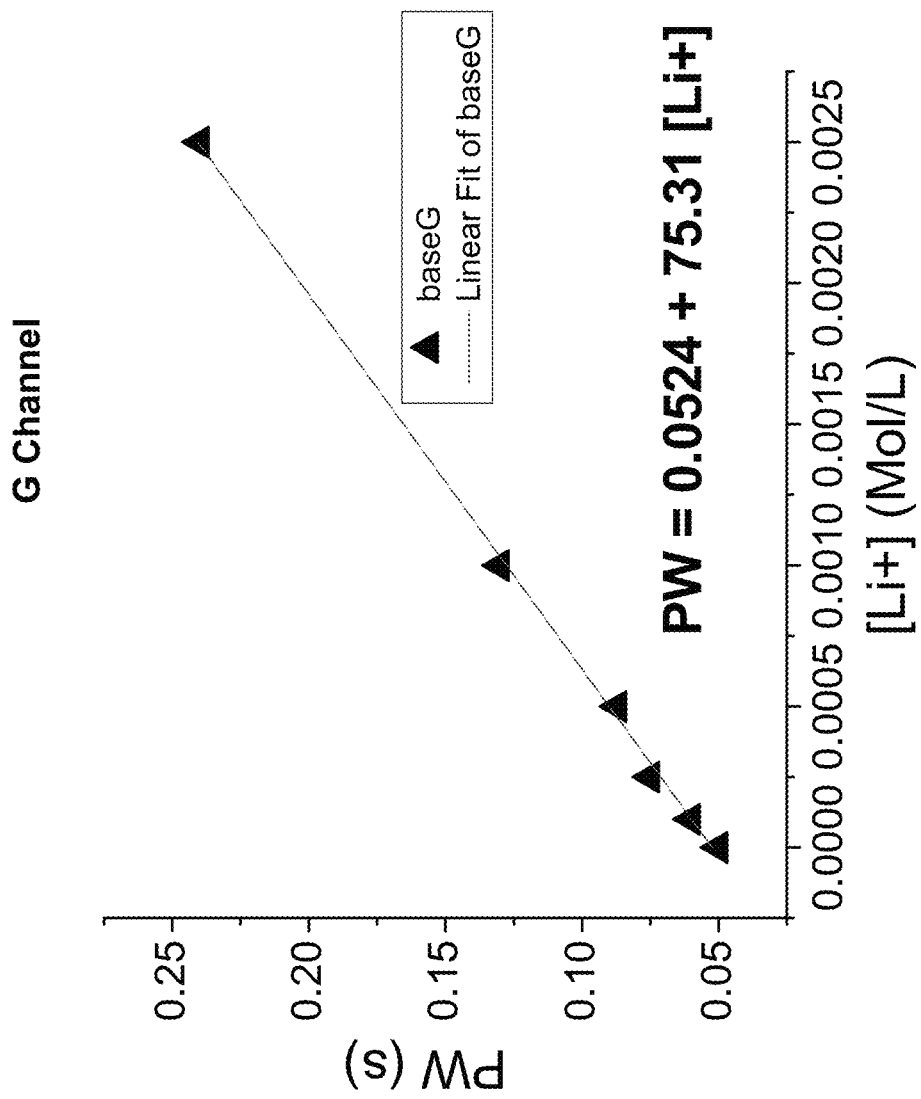
FIG. 4 shows a plot of pulse width versus Li+ concentration for the optical channel corresponding to the G nucleotide analog for reactions run with from 0 mM added Li+ to 2.5 mM Li+.

FIG. 4 shows a plot of pulse width versus Li+ concentration for the optical channel corresponding to the G nucleotide analog for reactions run with from 0 mM added Li+ to 2.5 mM Li+. The data show that the pulse width steadily increases with Li+ concentration. The increase in pulse width versus Li+ concentration exhibited a linear relationship over this range of concentration. Similar increases in pulse width were observed for the A, T, and C channels (not shown).

Figure 5:
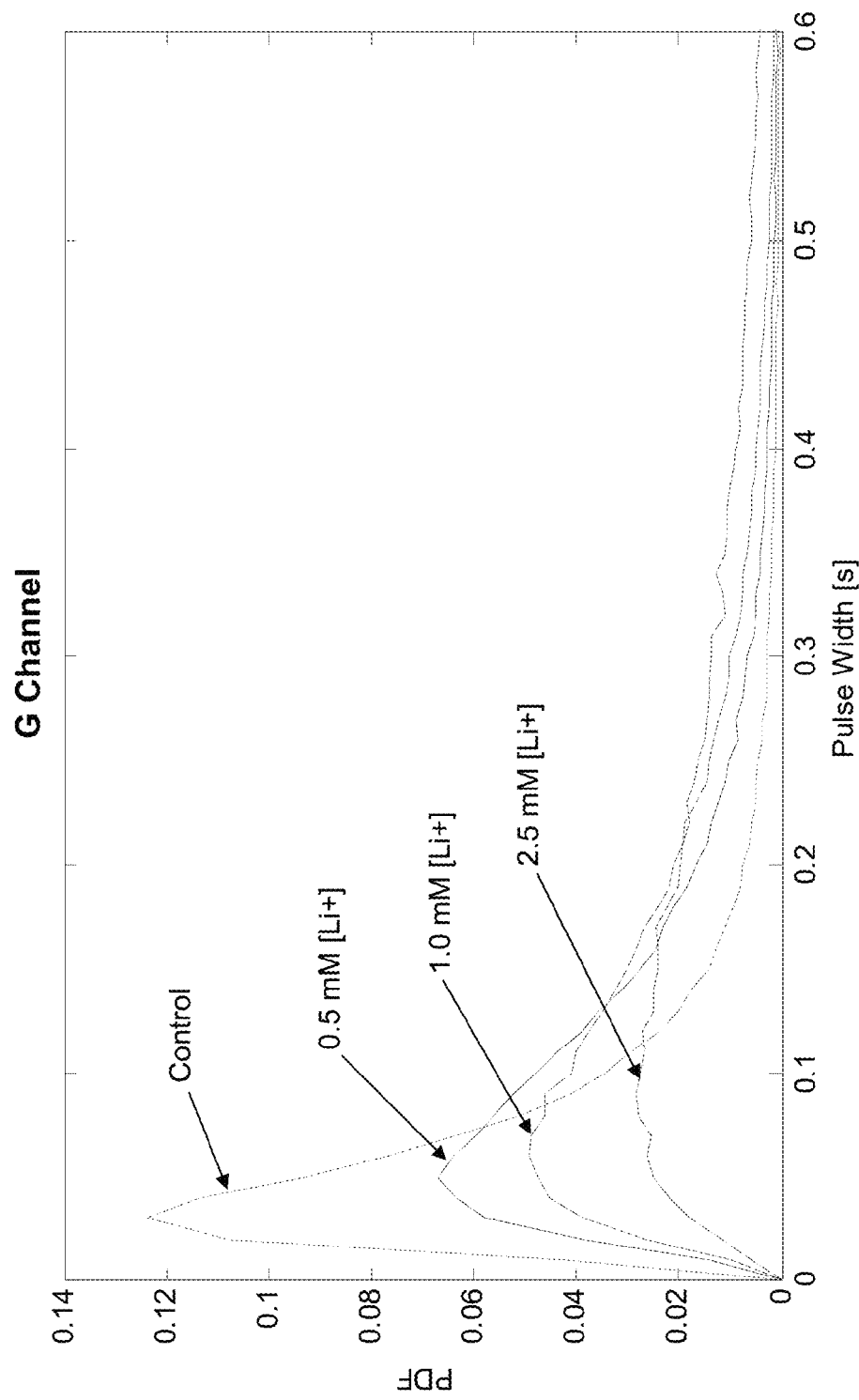
FIG. 5 shows a histogram of pulse width for the G channel across the array of zero mode waveguides illustrating how the median pulse width increases as the lithium concentration is increased from 0 mM, to 2.5 mM.

FIG. 5 shows a histogram of pulse width for the G channel across the array of zero mode waveguides illustrating how the median pulse width increases as the lithium concentration is increased from 0 mM, to 2.5 mM. Similar behavior was seen in the A, T, and C channels (not shown).

Figure 6:
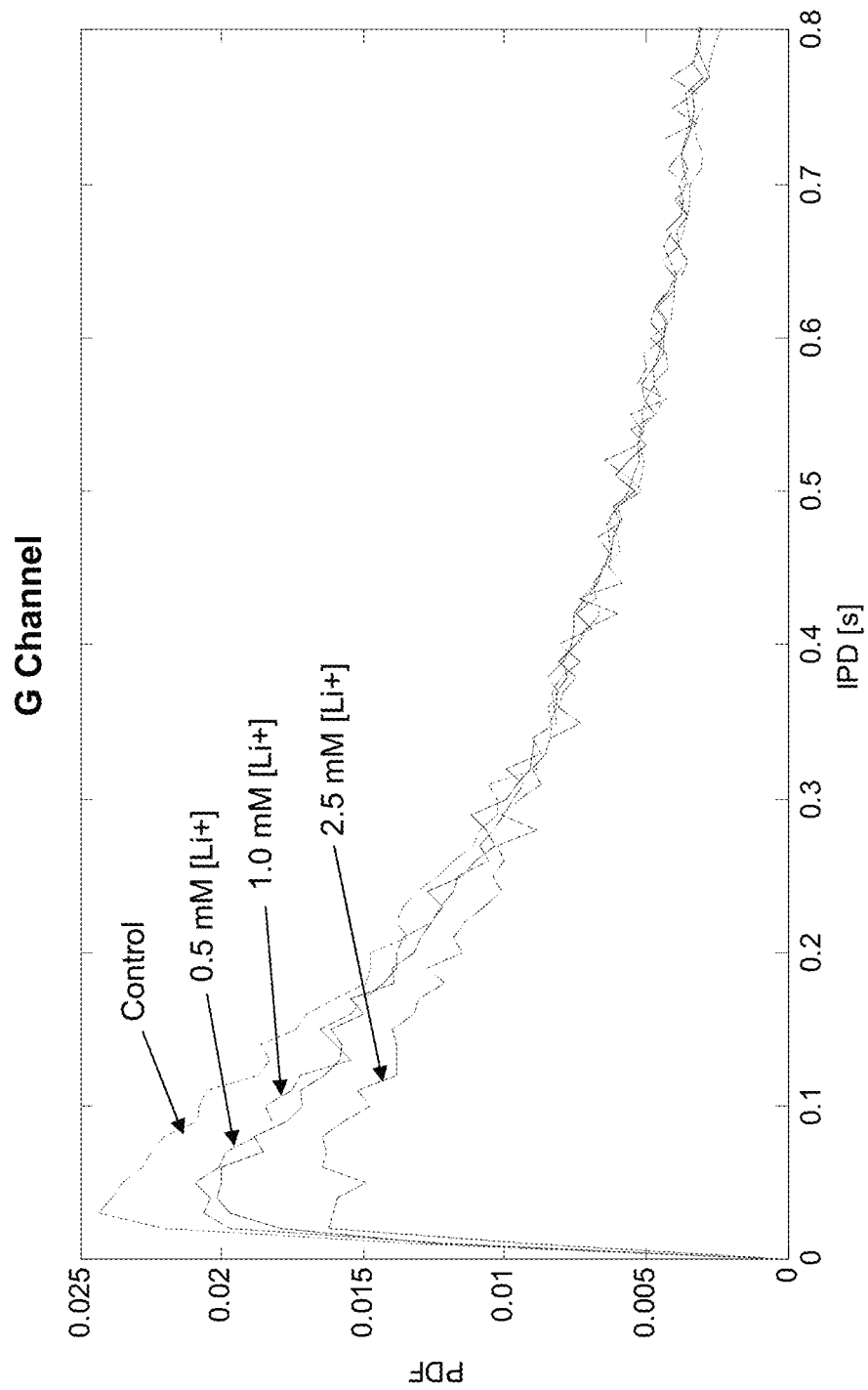
FIG. 6 shows a histogram for interpulse distance (IPD) across the array of zero mode waveguides.

FIG. 6 shows a histogram for interpulse distance (IPD) across the array of zero mode waveguides. It can be seen that while there is a change in interpulse distance with increasing amounts of Li+ from 0 mM, to 2.5 mM, the amount of change in IPD is smaller than for the change in pulse width.

Table 1 shows data for pulse width, interpulse distance, read length, and accuracy for a set of sequencing experiments. The pulse width and interpulse distance are shown for each of the four channels corresponding to the four nucleotide analogs.

TABLE 1

| PW, IPD, Read Length, and Accuracy at various [Li+] concentrations | | | | | | | | | | |
|---|---|---|---|---|---|---|---|---|---|---|
| [Li+] mM | PW1 sec | PW2 sec | PW3 sec | PW4 sec | IPD1 sec | IPD2 sec | IPD3 sec | IPD4 sec | RL bases | Acc % |
| cntrl | 0.107 | 0.104 | 0.085 | 0.121 | 0.694 | 0.901 | 0.679 | 0.585 | 410 | 82.73 |
| 0.5 | 0.159 | 0.146 | 0.120 | 0.169 | 0.755 | 1.186 | 0.785 | 0.665 | 339 | 84.26 |
| 1.0 | 0.207 | 0.187 | 0.147 | 0.204 | 0.800 | 1.183 | 0.785 | 0.706 | 306 | 84.25 |
| 2.5 | 0.394 | 0.336 | 0.231 | 0.317 | 0.880 | 1.518 | 0.966 | 0.897 | 254 | 82.09 |

Table 2 shows data for pulse width, interpulse distance, read length, and accuracy for a set of sequencing experiments.

TABLE 2

| PW, IPD, Read Length, and Accuracy at various [Li+] concentrations | | | | | | | | | | |
|---|---|---|---|---|---|---|---|---|---|---|
| [Li+] mM | PW1 sec | PW2 sec | PW3 sec | PW4 sec | IPD1 sec | IPD2 sec | IPD3 sec | IPD4 sec | RL bases | Acc % |
| cntrl | 0.094 | 0.095 | 0.082 | 0.121 | 0.713 | 0.977 | 0.743 | 0.594 | 401 | 83.89 |
| 0.1 | 0.110 | 0.109 | 0.091 | 0.138 | 0.686 | 0.989 | 0.696 | 0.597 | 389 | 84.23 |
| 0.25 | 0.124 | 0.120 | 0.100 | 0.152 | 0.696 | 1.020 | 0.715 | 0.608 | 359 | 84.21 |
| 0.5 | 0.132 | 0.128 | 0.107 | 0.161 | 0.685 | 1.068 | 0.766 | 0.623 | 338 | 83.67 |

Example 2

Single-Molecule Sequencing in Zero-Mode Waveguides with Na+

Sequencing reactions are carried out as described in Example 1, but various amounts of Na+ were present. Na+ was added in the form of sodium acetate. In one set of experiments, four reactions were carried out, a control with no added Na+, and the other three having 5 mM, 10 mM, and 20 mM of Na+ respectively. Table 3 shows data for pulse width, interpulse distance, read length, and accuracy for a set of sequencing experiments. The pulse width and interpulse distance are shown for each of the four channels corresponding to the four nucleotide analogs.

TABLE 3

| PW, IPD, Read Length, and Accuracy at various [Na+] concentrations | | | | | | | | | | |
|---|---|---|---|---|---|---|---|---|---|---|
| [Na+] mM | PW1 sec | PW2 sec | PW3 sec | PW4 sec | IPD1 sec | IPD2 sec | IPD3 sec | IPD4 sec | RL bases | Acc % |
| cntrl | 0.088 | 0.084 | 0.080 | 0.109 | 0.584 | 0.768 | 0.602 | 0.493 | 576 | 87.12 |
| 5 | 0.103 | 0.094 | 0.093 | 0.128 | 0.561 | 0.758 | 0.561 | 0.482 | 520 | 88.25 |
| 10 | 0.122 | 0.108 | 0.109 | 0.145 | 0.634 | 0.791 | 0.621 | 0.577 | 484 | 88.37 |
| 20 | 0.150 | 0.127 | 0.129 | 0.166 | 0.613 | 0.885 | 0.616 | 0.517 | 488 | 89.09 |

Example 3

Single-Molecule Sequencing in Zero-Mode Waveguides with Na+ and Li+

The experiments described above show that Li+ and Na+ have similar effects on pulse width, but that the amount of Na+ required for a similar effect is about 40 times higher than the amount of Li+. Single molecule sequencing runs were carried out as described above having both Li+ and Na+, and the experiments showed that Li+ and Na+ can be used together, and that the effects of the two salts together was cumulative.

Example 4

Stopped Flow Assays

The stopped flow analyses are carried out as described in published U.S. Patent Application 2009/0286245. A modified Φ29 DNA polymerase as described in published U.S. Patent Application No. 2007-0196846 at 100 nM was incubated with an oligonucleotide primer-template complex (100 nM) in a buffer solution as indicated for each individual experiment. This solution was rapidly mixed with a solution containing Alexa Fluor 555-dC6P, catalytic metal, and varying concentrations monovalent cation (acetate as the counter ion) using a SF-2004 stopped flow instrument (Kintek Corporation, Austin, Tex.). The oligonucleotide template was labeled with a fluorescent dye that is excited at 488 nm and the fluorescence emission was monitored at 515 nm using a band pass filter. Upon mixing and subsequent binding of the fluorescently labeled nucleotide to the enzyme-DNA complex, FRET between the dye on the DNA template and the dye on the nucleotide results in quenching of the dye on the template which causes a decrease in the fluorescent signal measured at 515 nm. After incorporation of the nucleotide and subsequent release of the generated polyphosphate-dye molecule from the enzyme-DNA complex, the fluorescent signal increased. The observed fluorescent trace was fit using a double exponential equation ($y = A_1 e^{-k_1 t} + A_2 e^{-k_2 t} + c$) to extract the observed rate of nucleotide binding and the observed rate of incorporation. The experiment was performed with the addition of the indicated concentration of alkai metal salts.

Example 5

Stopped Flow Analysis of KOAc and NaOAc

A stopped-flow analysis of a single turnover incorporation reaction comparing 120 mM KOAc to 120 mM NaOAc was carried out as described above. The conditions for this experiment were as follows: 50 mM ACES buffer at pH 6.5, 120 mM of monovalent salt, 120 mM of DTT, and 50 nM Polymerase Enzyme/DNA complex. This solution was mixed rapidly with 2 μM A555-6C-dC6P and 0.5 mM MnCl2 in the same buffer without enzyme/DNA. The data was best fit using a double exponential equation to obtain observed rates for binding and nucleotide incorporation (chemistry). For K+ the observed binding rate was 64.3 (error 0.63), and the observed rate of incorporation was 5.61 (error 0.045). For Na+ the observed binding rate was 48.1 (error 0.53), and the observed rate of incorporation was 1.26 (error 0.016). The difference represents approximately a 4.5 fold drop in the rate of incorporation which could be expected to greatly increase the detectability of pulses in single molecule sequencing.

Example 6

Apparent Rate of Binding and Chemistry for Li+, Na+, K+, Rb+, and Cs+

Figure 7:
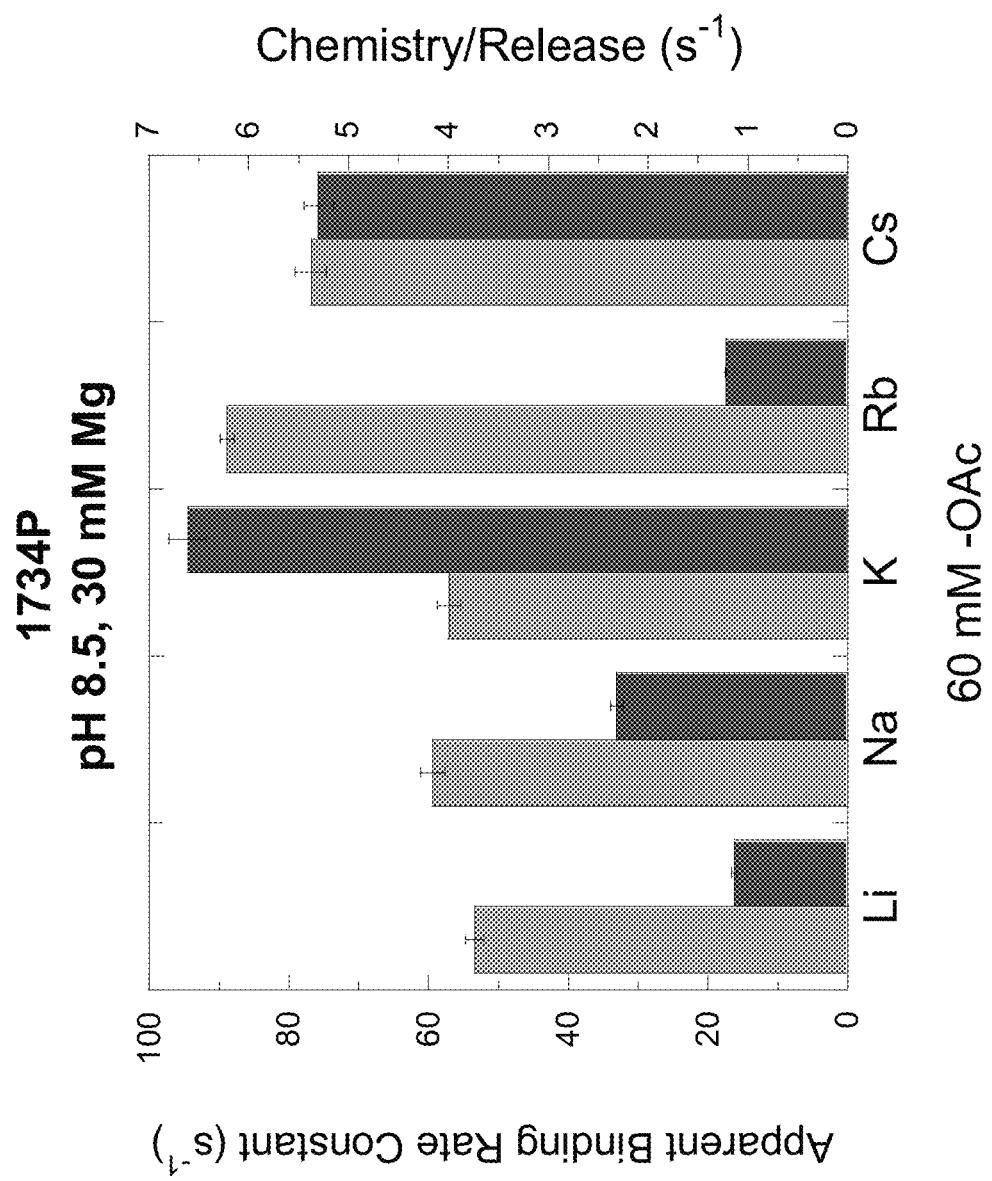
FIG. 7 shows a bar chart showing the apparent rate of binding and apparent rate of chemistry for Li+, Na+, K+, Rb+, and Cs+.

FIG. 7 is a bar chart showing the apparent rate of binding and apparent rate of chemistry for Li+, Na+, K+, Rb+, and Cs+. For these data the stopped flow fluorescence trace was fit the double exponential equation. The apparent binding rate constant is plotted on the left axis (light) and the apparent rate of the chemistry/release step is plotted on the right axis (dark). The conditions for this experiment were as follows: 50 mM TRIS pH 8.5 buffer, 60 mM of monovalent salt, 120 mM DTT, 60 nM of polymerase enzyme/DNA complex. This solution was mixed rapidly with 3 μM A555-6C-dC6P and 30 mM MgCl2 in the same buffer without enzyme/DNA.

Example 7

Figure 8:
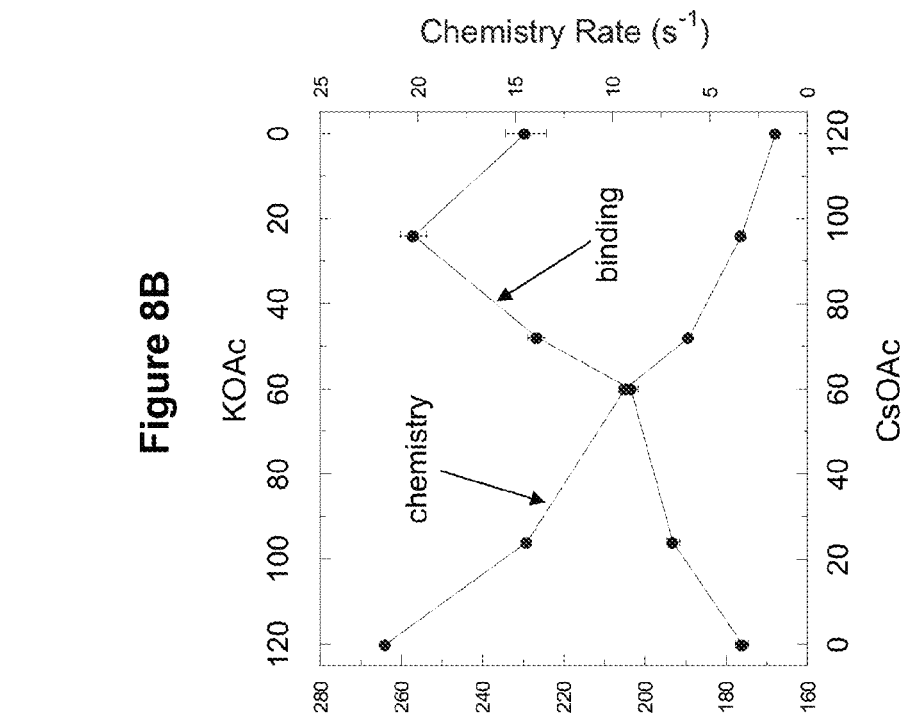
FIG. 8A shows the apparent rate constant of the binding reaction (k1 s-1, left axis) and the apparent rate constant for the binding/chemistry reaction (k2 s-1, right axis) as a function of the CsOAc concentration.
FIG. 8B shows the apparent rate constant of the binding reaction (k1 s-1, left axis) and the apparent rate constant for the binding/chemistry reaction (k2 s-1, right axis) as a function of the CsOAc concentration where concentration of alkali metal cation is kept constant using varying amounts of KOAc.
Figure 8:
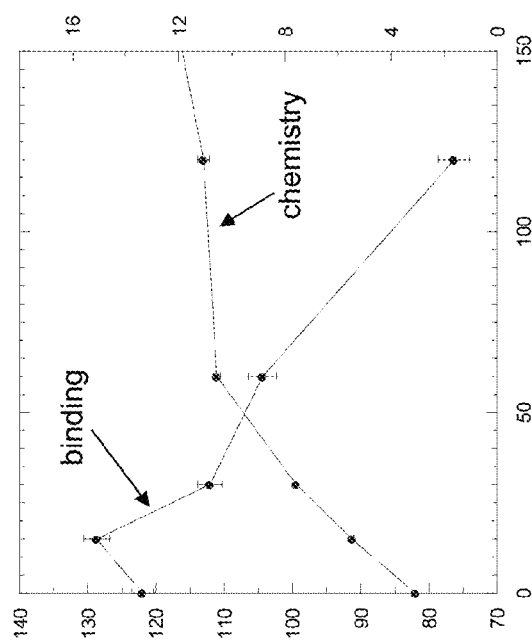

Apparent Rate of Binding and Chemistry for Cs+ as a Function of Concentration In FIG. 8(A) the apparent rate constant of the binding reaction (k1 s-1, left axis) and the rate constant for the apparent binding/chemistry reaction (k2 s-1, right axis) is plotted as a function of the CsOAc concentration. The conditions for this experiment were as follows: 50 mM TRIS pH 8.5 buffer, varying CsOAc salt as indicated, 120 mM DTT, and 60 nM polymerase enzyme/DNA complex. This solution was mixed rapidly with 3 μM A555-6C-dC6P and 30 mM MgCl2 in the same buffer without enzyme/DNA. The data indicate that binding saturation behavior could be present.

In FIG. 8(B) the Cs+ concentration is changed while the overall concentration of alkali metal cation is kept constant using varying amounts of K+. The apparent rate constant of the binding reaction (k1 s-1, left axis) and the apparent rate constant for the binding/chemistry reaction (k2 s-1, right axis) is plotted as a function of the CsOAc concentration (bottom axis) and KOAc (top axis). The total salt concentration is constant at 120 mM and only the mole fraction of K versus Cs is being varied. The conditions for this experiment were as follows: 50 mM ACES pH 6.5 buffer, 120 mM monovalent salt, 120 mM DTT, and 60 nM polymerase enzyme/DNA complex. This solution was mixed rapidly with 3 μM A555-6C-dC6P and 1.5 mM MnCl2 in the same buffer without enzyme/DNA. These data confirm that the changes in the rate of binding and chemistry is due to the identity and amount of the cation, and not due, for example to the amount of the acetate anion. The modulation of the on rate by the Cs+ implies that the IPD could be increased or decreased relative to potassium ion by the addition of monovalent cations. This control can be advantageous to pulse detection.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

We claim:

1. A method for performing single molecule sequencing having a pulse width within a desired range comprising:
   providing a composition comprising:
   a modified recombinant phi-29 type DNA polymerase enzyme having at least 80% sequence similarity to SEQ ID NO: 1, a primer, a template nucleic acid, and a plurality of labeled nucleotide analogs, wherein the composition comprises Li+ at a concentration of from about 0.05 mM to about 40 mM; and
   observing the association of the labeled nucleotide analogs with a complex of the polymerase, primer, and template nucleic acid over time to determine a sequence of the template nucleic acid, wherein the concentration of Li+ is selected such that the single molecule sequencing reaction has a median pulse width from about 10 msec to about 400 msec.

2. The method of claim 1 wherein the single molecule sequencing reaction has a median interpulse distance from about 300 msec to about 1.5 s.

3. The method of claim 1 wherein the single molecule sequencing reaction has a median read length greater than 300 bases.

4. The method of claim 1 wherein the concentration of Li+ is from about 0.1 mM to about 4 mM.

5. The method of claim 1 wherein the composition further comprises K+ at a concentration from about 100 mM to about 400 mM.

6. The method of claim 5 wherein the concentration of K+ is from about 150 mM to about 250 mM.

7. The method of claim 1 wherein the polymerase enzyme, primer, and template nucleic acid comprise a polymerase complex that is immobilized on a surface.

8. The method of claim 7 wherein the polymerase complex is immobilized onto the surface by attachment to the surface of the polymerase enzyme or the template nucleic acid.

9. The method of claim 7 wherein the polymerase enzyme complex is immobilized within a confined volume.

10. The method of claim 7 wherein the polymerase complex is immobilized in a zero mode waveguide.

11. The composition of claim 1 wherein the plurality of nucleotide analogs are labeled on the phosphate portion such that the label dissociates upon incorporation into the growing strand.

12. The method of claim 1 wherein the plurality of labeled nucleotide analogs are labeled such that the label is cleaved upon incorporation of the nucleotide analog into the growing strand, the observed pulses corresponding to the time period when the labeled nucleotide analog is associated with the polymerase enzyme complex.

13. The method of claim 12 wherein the polymerase enzyme complex is immobilized onto a substrate.

14. The method of claim 13 wherein the polymerase enzyme complex is immobilized within a confined volume.

15. The method of claim 13 wherein the confined volume comprises a zero mode waveguide.

16. The method of claim 1 wherein the observing is carried out using optical detection.

17. The method of claim 1 wherein the plurality of labeled nucleotide analogs comprise fluorescent or fluorogenic moieties.

18. The method of claim 1 wherein the plurality of labeled nucleotide analogs comprise fluorescent labels.

* * * * *

```
                            SEQUENCE LISTING

<160> NUMBER OF SEQ ID NOS: 1

<210> SEQ ID NO 1
<211> LENGTH: 575
<212> TYPE: PRT
<213> ORGANISM: Bacteriophage phi-29

<400> SEQUENCE: 1

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335
```

-continued

```
Lys Glu His Tyr Asp Leu Tyr Asn Val Glu Tyr Ile Ser Gly Leu Lys
            340                 345                 350
Phe Lys Ala Thr Thr Gly Leu Phe Lys Asp Phe Ile Asp Lys Trp Thr
            355                 360                 365
Tyr Ile Lys Thr Thr Ser Glu Gly Ala Ile Lys Gln Leu Ala Lys Leu
            370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
            420                 425                 430
Ile Thr Ala Trp Ala Arg Tyr Thr Thr Ile Thr Ala Ala Gln Ala Cys
            435                 440                 445
Tyr Asp Arg Ile Ile Tyr Cys Asp Thr Asp Ser Ile His Leu Thr Gly
            450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
            485                 490                 495
Gln Lys Thr Tyr Ile Gln Asp Ile Tyr Met Lys Glu Val Asp Gly Lys
            500                 505                 510
Leu Val Glu Gly Ser Pro Asp Asp Tyr Thr Asp Ile Lys Phe Ser Val
            515                 520                 525
Lys Cys Ala Gly Met Thr Asp Lys Ile Lys Lys Glu Val Thr Phe Glu
            530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys
                565                 570                 575
```